(12) United States Patent
Colak et al.

(10) Patent No.: US 9,556,340 B2
(45) Date of Patent: Jan. 31, 2017

(54) POLYOXAZOLINE COPOLYMERS

(71) Applicant: 3M INNOVATIVE PROPERTIES COMPANY, St. Paul, MN (US)

(72) Inventors: Semra Colak, Saint Louis Park, MN (US); Paul B. Armstrong, Minneapolis, MN (US); Michael J. Svarovsky, Granger, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/649,400

(22) PCT Filed: Dec. 11, 2013

(86) PCT No.: PCT/US2013/074259
§ 371 (c)(1),
(2) Date: Jun. 3, 2015

(87) PCT Pub. No.: WO2014/099518
PCT Pub. Date: Jun. 26, 2014

(65) Prior Publication Data
US 2015/0307718 A1    Oct. 29, 2015

Related U.S. Application Data

(60) Provisional application No. 61/739,162, filed on Dec. 19, 2012.

(51) Int. Cl.
*C09D 5/16* (2006.01)
*C09D 5/00* (2006.01)
(Continued)

(52) U.S. Cl.
CPC ............... *C09D 5/16* (2013.01); *A01N 55/00* (2013.01); *C08F 222/10* (2013.01); *C09D 5/00* (2013.01); *C09D 5/1681* (2013.01)

(58) Field of Classification Search
CPC ........... C09D 5/16; C09D 5/00; C09D 5/1681; C08F 222/10; A01N 55/00
(Continued)

(56) References Cited

U.S. PATENT DOCUMENTS 4,552,908 A * 11/1985 Nicks .................. C09D 5/02
523/504
4,958,005 A * 9/1990 Saegusa .............. C08G 73/0233
525/410
(Continued)

FOREIGN PATENT DOCUMENTS

EP      0136025     4/1985
EP      0244828     11/1987
(Continued)

OTHER PUBLICATIONS

Banerjee, "Antifouling Coatings: Recent Developments in the Design of Surfaces That Prevent Fouling by Proteins, Bacteria, and Marine Organisms", Advanced Materials, 2011, vol. 23, pp. 690-718.

"Biofouling Prevention Coatings," Office of Naval Research [online], retrieved from the internet Sep. 14, 2015, http://www.onr.navy.mil/en/Media-Center/Fact-Sheets/Biofouling-Prevention.aspx, p. 1-2.

Buckingham-Meyer, "Comparative evaluation of biofilm disinfectant efficacy tests", Journal of Microbiological Methods, 2007, vol. 70, pp. 236-244.

Chatelier, "Quantitative Analysis of Polymer Surface Restructuring", Langmuir, 1995, vol. 11, No. 7, pp. 2576-2584.

Chen, "A New Avenue to Nonfouling Materials", Adv. Mater., 2008, vol. 20, pp. 335-338.

(Continued)

*Primary Examiner* — Michael M Bernshteyn
(74) *Attorney, Agent, or Firm* — Julie Lapos-Kuchar; Jean Lown

(57) ABSTRACT

A copolymer derived from a monomer mixture that includes monomers having the formulas: (A) and (B) wherein: Q is O or N; $R^{10}$ is H or $CH_3$; $R^{11}$ is an organic group comprising a hydrolyzable silyl group; $R^{12}$ is H or $CH_3$; P is: (I); $R^1$ is selected from H, an alkyl group, an aryl group, and a combination thereof; $R^2$ is selected from an alkyl group, an aryl group, a combination thereof, and a $R^f$—Y—$(CH_2)_x$— group; $R^f$ is a perfluorinated alkyl group; Y is selected from a bond, —S(O)$_2$—N(CH$_3$)—, —S(O)$_2$—N(CH$_2$CH$_3$)—, —S(O)$_2$—O—, —S(O)$_2$—, —C(O)—, —C(O)—S—, —C(O)—O—, —C(O)—NH—, —C(O)—N(CH$_3$)—, —C(O)—N(CH$_2$CH$_3$)—, —(CH$_2$CH$_2$O)$_y$—, —O—, and —O—C(O)—CH=CH—C(O)—O—; n is an integer of greater than 2; x is an integer of at least 2; and y is an integer of at least 1.

20 Claims, No Drawings

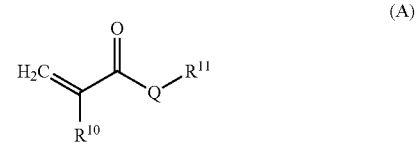
(A)

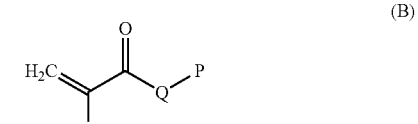

(B)

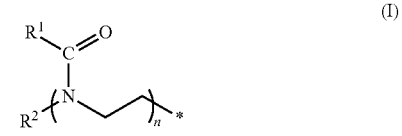

(I)

(51) Int. Cl.
A01N 55/00 (2006.01)
C08F 222/10 (2006.01)

(58) Field of Classification Search
USPC ............................................ 524/547
See application file for complete search history.

(56) References Cited

U.S. PATENT DOCUMENTS

| | | | |
|---|---|---|---|
| 5,219,662 | A | 6/1993 | Grimminger |
| 6,162,877 | A * | 12/2000 | Sau .................... C08G 83/00 525/326.9 |
| 6,974,856 | B1 * | 12/2005 | Kataoka ........... C08G 65/33317 525/412 |
| 7,585,919 | B2 | 9/2009 | Pocius |
| 2005/0106208 | A1 | 5/2005 | Neff |
| 2007/0254979 | A1 | 11/2007 | Salz |
| 2008/0185332 | A1 | 8/2008 | Niu |
| 2009/0004241 | A1 | 1/2009 | Ho |

FOREIGN PATENT DOCUMENTS

| | | | |
|---|---|---|---|
| EP | 0616256 | | 9/1994 |
| EP | 1219661 | | 7/2002 |
| EP | 1897626 | | 3/2008 |
| FR | 2941971 | | 8/2013 |
| GB | EP 0136025 | A2 * | 4/1985 ............... C09D 5/02 |
| JP | EP 0244828 | A2 * | 11/1987 ......... C08G 73/0233 |
| JP | EP 1219661 | A1 * | 7/2002 ....... C08G 65/33317 |
| KR | 2009-0126796 | | 12/2009 |
| WO | WO 00-34361 | | 6/2000 |
| WO | WO 00-37541 | | 6/2000 |
| WO | WO 0034361 | A1 * | 6/2000 ............. C08G 83/00 |
| WO | WO 2010-089484 | | 8/2010 |
| WO | WO 2013-000478 | | 1/2013 |
| WO | WO 2013-123507 | | 8/2013 |
| WO | WO 2014-099465 | | 6/2014 |

OTHER PUBLICATIONS

Cheng, "Inhibition of bacterial adhesion and biofilm formation on zwitterionic surfaces", Biomaterials, 2007, vol. 28, pp. 4192-4199.
Darouiche, "Treatment of Infections Associated with Surgical Implants", N. Engl J. Med., Apr. 2004, vol. 350, No. 14, pp. 1422-1429.
Hall-Stoodley, "Bacterial biofilms: From the natural environment to infectious diseases", Nature Reviews, Microbiology, 2004, vol. 2, pp. 95-108.
Holmlin, "Zwitterionic SAMs that Resist Nonspecific Adsorption of Protein from Aqueous Buffer", Langmuir, 2001, vol. 17, No. 9, pp. 2841-2850.
Hoogenboom, "Poly (2-oxazoline)s: A Polymer Class with Numerous Potential Applications", Agnew. Chem. Int. Ed., 2009, vol. 48, pp. 7978-7994.
Hucknall, "In Pursuit of Zero: Polymer Brushes that Resist the Adsorption of Proteins", Adv. Mater., 2009, vol. 21, pp. 2441-2446.
Ivanova, "Micellar Structures of Hydrophilic/Lipophilic and Hydrophilic/Fluorophilic Poly(2-oxazoline) Diblock Copolymers in Water", Macromol. Chem. Phys., 2008, vol. 209, pp. 2248-2258.

Kaku, "New Fluorinated Oxazoline Block Copolymer Lowers the Adhesion of Platelets on Polyurethane Surfaces," Journal of Polymer Science: Part A: Polymer Chemistry, 1994, vol. 32, pp. 2187-2192.
Kane, "Kosmotropes Form the Basis of Protein-Resistant Surfaces", Langmuir, 2003, vol. 19, No. 6, pp. 2388-2391.
Knetsch, "New Strategies in the Development of Antimicrobial Coatings: The Example of Increasing Usage of Silver and Silver Nanoparticles", Polymers, 2011, vol. 3, pp. 340-366.
Kobayashi, "Synthesis of a Nonionic Polymer Surfactant from Cyclic Imino Ethers by the Initiator Method", Macromolecules, 1987, vol. 20, No. 8, pp. 1729-1734.
Kobayashi, "Synthesis of Acryl- and Methacryl-Type Macromonomers and Telechelics by Utilizing Living Polymerization of 2-Oxazolines," Macromolecules, 1989, vol. 22, No. 7, pp. 2878-2884.
Konradi, "Poly-2-methyl-2-oxazoline: A Peptide-like Polymer for Protein-Repellant Surfaces," Langmuir, 2008, vol. 24, pp. 613-616.
Krishnan, "Advances in polymers for anti-biofouling surfaces", J. Mater. Chem., 2008, vol. 18, pp. 3405-3413.
Ma, "Surface-Initiated Atom Transfer Radical Polymerization of Oligo (ethylene glycol) Methyl Methacrylate from a Mixed Self-Assembled Monolayer on Gold", Adv. Funct. Mater., 2006, vol. 16, pp. 640-648.
Madkour, "Fast Disinfecting Antimicrobial Surfaces", Langmuir, 2009, vol. 25, No. 2, pp. 1060-1067.
Miyamoto, "Novel Covalent-Type Electrophilic Polymerization of 2-(Perfluoroalkyl)-2-oxazolines Initiated by Sulfonates," Macromolecules, 1991, vol. 24, No. 1, pp. 11-16.
Miyamoto, "Preperation of Poly [(N-acetylimino) ethylene] Having (Perfluoroacylimino) ethyl End Group and Its Surface Activity," Polymer Journal, 1995, vol. 27, No. 5, pp. 461-468.
Mrksich, "A Surface Chemistry approach to studying cell adhesion", Chem. Soc. Rev., 2000, vol. 29, pp. 267-273.
Ostuni, "A Survey of Structure—Property Relationships of Surfaces that Resist the adsorption of Protein", Langmuir, 2001, vol. 17, No. 18, pp. 5605-5620.
Prime, "Adsorption of Proteins onto Surfaces Containing End-Attached Oligo (ethylene oxide): A Model System Using Self—Assembled Monolayers", J. Am. Chem. Soc., 1993, vol. 115, No. 23, pp. 10714-10721.
Ramsden, "Puzzles and Paradoxes in Protein Adsorption", J. Chem Soc. Rev., 1995, vol. 24, pp. 73-78.
Shen, "PEO-like plasma polymerized tetraglyme surface interactions with leukocytes and proteins: in vitro and in vivo studies", J. Biomater. Sci. Polymer. Edn., 2002, vol. 13, No. 4, pp. 367-390.
Weberskirch, "Design and synthesis of a two compartment micellar system based on the self-association behavior of poly (N-acylethyleneimine) end-capped with a fluorocarbon and a hydrocarbon chain", Macromol. Chem. Phys., 2000, vol. 201, No. 10, pp. 995-1007, XPO55109078, ISSN: 1022-1352.
Werner, "Current Strategies towards hemocompatible coatings", J. Mater. Chem., 2007, vol. 17, pp. 3376-3384.
Yang, "Pursuing "Zero" Protein Adsorption of Poly (Carboxybetain) from Undiluted Blood Serum and Plasma", Langmuir, 2009, vol. 25, No. 19, pp. 11911-11916.
International Search report for PCT International Application No. PCT/US2013/074259 mailed on Jul. 22, 2014, 4 pages.

* cited by examiner

POLYOXAZOLINE COPOLYMERS

CROSS REFERENCE TO RELATED APPLICATIONS

This application is a national stage filing under 35 U.S.C. 371 of PCT/US2013/074259, filed Dec. 11, 2013, which claims priority to U.S. Provisional Application No. 61/739,162, filed Dec. 19, 2012, the disclosure of which is incorporated by reference in their entirety herein.

BACKGROUND

Prevention of biofouling remains a challenging problem in numerous areas. These include, but are not limited to, biomedical applications, marine coating technologies, water filtration, transport, and storage systems. Undesirable consequences of this ubiquitous problem can include reduction in the efficacy/sensitivity of devices, operational losses, thrombosis, as well as microbial infections. Therefore, the development of new technologies and materials that reduce or completely prevent any undesired deposition of microorganisms is of great importance. However, tailoring an efficient non-fouling material requires understanding the interactions involved, which is hindered by the complexity of the process, making it challenging to provide solutions to the problem.

Biofilm formation generally starts within seconds following implantation of a given material (e.g., medical implant) in aqueous environments, such as blood, municipal and/or sea water. While biofilms can be formed by a single species, often they are composed of a community of different types of microorganisms. The first step of the process is often the adsorption of proteins on the substrate surface, which is followed by adsorption of a cascade of larger, more complex species that include microorganisms such as bacteria, fungi, and algae. Thus, one can argue that the larger microorganisms rarely interact with the clean surface but rather with the proteins adsorbed on it. One approach that has been employed to prevent the biofoulmg process is the incorporation of antimicrobially active ingredients into materials. This can be done by blending actives into the material during its manufacture, covalently attaching an active agent to the surface of the material, or coating/painting an antimicrobial onto a surface such that it can subsequently leach from the material. However, once a certain amount of organic material (e.g., cell debris) has formed, the surface activity decreases as the active material can no longer reach its target. An alternative approach is to prevent biofoulmg by preventing the attachment of a broad range of species, rather than killing them.

A key challenge in preventing biofilm formation is the design of smart materials or engineered surfaces that can effectively resist the irreversible attachment of a wide variety of species including proteins, microbial cells, and spores. Many approaches have been investigated, and hydrophilic modification of surfaces using polyethylene glycol) (PEG) and zwitterionic polymers with high wettability are among the most promising. However, larger microorganisms as well as proteins are inherently amphiphilic. They operate by different attachment mechanisms, with some having higher attachment affinity to hydrophobic surfaces and others to hydrophilic surfaces. Therefore, a desirable antifouling coating can be defined as one that can show stealth behavior against multiple species. With these findings, there is increasing demand for engineered materials, particularly amphiphilic materials, which, similar to living organisms, can restructure their surfaces depending on the environment. However, one should be aware that a delicate balance of hydrophilicity to hydrophobicity (or amphiphilicity) should be met for a particular surface/coating to be effective in prevention of biofilm formation across a wide variety of species.

SUMMARY

The present disclosure provides polyoxazoline (POx) copolymers. More specifically, the disclosure provides novel copolymers, and in certain embodiments, amphiphilic copolymers, where polyoxazolines are employed as the hydrophilic component and a perfluorinated group is employed as the hydrophobic component. Copolymers of the present disclosure are useful in making coatings that resist biofilm formation or that enhance the release of formed biofilms.

In one embodiment, the present disclosure provides a copolymer derived from a monomer mixture that includes monomers having the formulas:

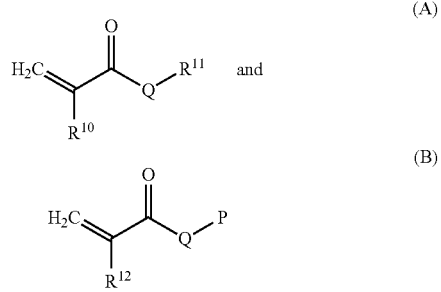

wherein: Q is O or N; $R^{10}$ is H or $CH_3$; $R^{11}$ is an organic group that includes a hydrolyzable silyl group; $R^{12}$ is H or $CH_3$; P is:

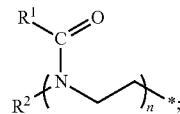

wherein: $R^1$ is selected from H, an alkyl group, an aryl group, and a combination thereof; $R^2$ is selected from an alkyl group, an aryl group, a combination thereof and a $R^f$—Y—$(CH_2)_x$— group; $R^f$ is a perfluorinated alkyl group; Y is selected from a bond, —S(O)$_2$—N(CH$_3$)—, —S(O)$_2$—N(CH$_2$CH$_3$)—, —S(O)$_2$—O—, —S(O)$_2$—, —C(O)—, —C(O)—S—, —C(O)—O—, —C(O)—NH—, —C(O)—N(CH$_3$)—, —C(O)—N(CH$_2$CH$_3$)—, —(CH$_2$CH$_2$O)$_y$—, —O—, and —O—C(O)—CH=CH—C(O)—O—; n is an integer of greater than 2; x is an integer of at least 2; and y is an integer of at least 1. In P, the (*) is the point of attachment to Q in Monomer B.

In one embodiment, the present disclosure provides a brush copolymer derived from a monomer mixture that includes monomers having the formulas:

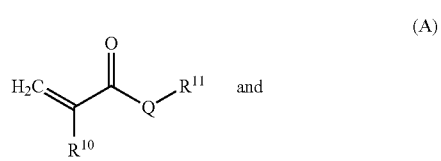

(B)

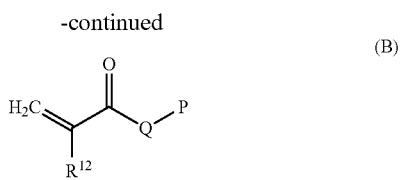

wherein: Q is O or N; $R^{10}$ is H or $CH_3$; $R^{11}$ is —Z—Si$(R^{13})_3$; $R^{12}$ is H or $CH_3$; each $R^{13}$ is independently selected from an alkyl group, an aryl group, a combination thereof (i.e., alkaryl or aralkyl group), and a hydrolyzable group; at least one $R^{13}$ is a hydrolyzable group; Z is selected from an alkylene group, an arylene group, and a combination thereof (i.e., alkarylene or aralkylene), optionally including —O—, —C(O)—, —NH—, —S—, or a combination thereof, within the chain; P is:

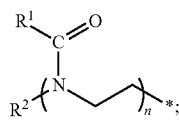

wherein: $R^1$ is selected from H, an alkyl group, an aryl group, and combinations thereof; $R^2$ is $R^f$—Y—$(CH_2)_x$— group; $R^f$ is a perfluorinated (C1-C8)alkyl group; Y is a bond, —S(O)$_2$—N(CH$_3$)—, —C(O)—O—, —C(O)—NH—, or —(CH$_2$CH$_2$O)$_y$—; n is an integer from 20 to 100; x is an integer from 2 to 20; and y is an integer from 1 to 20. In P, the (*) is the point of attachment to Q in Monomer B.

As used herein, the term "organic group" means a hydrocarbon group (with optional elements other than carbon and hydrogen, such as oxygen, nitrogen, sulfur, silicon, and halogens) that is classified as an aliphatic group, cyclic group, or combination of aliphatic and cyclic groups (e.g., alkaryl and aralkyl groups). In the context of the present invention, the organic groups are those that do not interfere with the formation of the copolymer. The term "aliphatic group" means a saturated or unsaturated linear or branched hydrocarbon group. This term is used to encompass alkyl, alkenyl, and alkynyl groups, for example. The term "alkyl group" is defined herein below. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" are defined herein below. The term "heterocyclic group" means a closed ring hydrocarbon in which one or more of the atoms in the ring is an element other than carbon (e.g., nitrogen, oxygen, sulfur, etc.). The organic group can have any suitable valency but is often monovalent or divalent.

The term "alkyl" refers to a monovalent group that is a radical of an alkane and includes straight-chain, branched, cyclic, and bicyclic alkyl groups, and combinations thereof, including both unsubstituted and substituted alkyl groups. Unless otherwise indicated, the alkyl groups typically contain from 1 to 30 carbon atoms. In some embodiments, the alkyl groups contain 1 to 20 carbon atoms, 1 to 10 carbon atoms, 1 to 6 carbon atoms, 1 to 4 carbon atoms, or 1 to 3 carbon atoms. Examples of alkyl groups include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, norbornyl, and the like.

The term "alkylene" refers to a divalent group thai is a radical of an aikane and includes groups that are linear, branched, cyclic, bicyclic, or a combination thereof. Unless otherwise indicated, the alkylene group typically has 1 to 30 carbon atoms. In some embodiments, the alkylene group has 1 to 20 carbon atoms, 1 to 10 carbon atoms, 1 to 6 carbon atoms, or 1 to 4 carbon atoms. Examples of alkylene groups include methylene, ethylene, 1,3-propylene, 1,2-propylene, 1,4-butylene, 1,4-cyclohexylene, and 1,4-cyclohexydimethylene.

The term "aromatic" refers to a group that is carbocyclic or heterocyclic and that is fully unsaturated.

The term "aryl" refers to a monovalent group that is aromatic and, optionally, carbocyclic. The aryl has at least one aromatic ring. Any additional rings can be unsaturated, partially saturated, saturated, or aromatic. Optionally, an aromatic ring can have one or more additional carbocyclic rings that are fused to the aromatic ring. Unless otherwise indicated, the aryl groups typically contain from 6 to 30 carbon atoms. In some embodiments, the aryl groups contain 6 to 20, 6 to 18, 6 to 16, 6 to 12, or 6 to 10 carbon atoms. Examples of an aryl group include phenyl, naphthyl, biphenyl, phenanthryl, and anthracyl.

The term "arylene" refers to a divalent group that is aromatic and, optionally, carbocyclic. The arylene has at least one aromatic ring. Any additional rings can be unsaturated, partially saturated, or saturated. Optionally, an aromatic ring can have one or more additional carbocyclic rings that are fused to the aromatic ring. Unless otherwise indicated, arylene groups often have 6 to 20 carbon atoms, 6 to 18 carbon atoms, 6 to 16 carbon atoms, 6 to 12 carbon atoms, or 6 to 10 carbon atoms.

The term "aralkyl" refers to a monovalent group that is an alkyl group substituted with an aryl group (e.g., as in a benzyl group). The term "alkaryl" refers to a monovalent group that is an aryl substituted with an alkyl group (e.g., as in a tolyl group). Unless otherwise indicated, for both groups, the alkyl portion often has 1 to 10 carbon atoms, 1 to 6 carbon atoms, or 1 to 4 carbon atoms and an aryl portion often has 6 to 20 carbon atoms, 6 to 18 carbon atoms, 6 to 16 carbon atoms, 6 to 12 carbon atoms, or 6 to 10 carbon atoms.

The term "aralkylene" refers to a divalent group that is an alkylene group substituted with an aryl group or an alkylene group attached to an arylene group. The term "alkarylene" refers to a divalent group that is an arylene group substituted with an alkyl group or an arylene group attached to an alkylene group. Unless otherwise indicated, for both groups, the alkyl or alkylene portion typically has from 1 to 20 carbon atoms, 1 to 10 carbon atoms, 1 to 6 carbon atoms, or 1 to 4 carbon atoms. Unless otherwise indicated, for both groups, the aryl or arylene portion typically has from 6 to 20 carbon atoms, 6 to 18 carbon atoms. 6 to 16 carbon atoms. 6 to 12 carbon atoms, or 6 to 10 carbon atoms.

The term "perfluorinated alkyl group" or "perfluoroalkyl group" refers to an alkane group having all C—H bonds replaced with C—F bonds.

The term "silyl" refers to a monovalent group of formula —Si$(R^c)_3$ where $R^c$ is a hydrolyzable group or a non-hydrolyzable group. In many embodiments, the silyl group is a "hydrolyzable silyl" group, which means that the silyl group contains at least one $R^c$ group that is a hydrolyzable group.

The term "hydrolyzable group" refers to a group that can react with water having a pH of 1 to 10 under conditions of atmospheric pressure. The hydrolyzable group is often converted to a hydroxyl group when it reacts. The hydroxyl group often undergoes further reactions such as condensation reactions. Typical hydrolyzable groups include, but are not limited to, alkoxy, aryloxy, aralkyloxy, alkaryloxy, acyloxy, or halo. As used herein, the term is often used in reference to one of more groups bonded to a silicon atom in a silyl group.

The term "non-hydrolyzable group" refers to a group that cannot react with water having a pH of 1 to 10 under conditions of atmospheric pressure. Typical non-hydrolyzable groups include, but are not limited to, alkyl, aryl, aralkyl, and alkaryl. As used herein, the term is often used in reference to one or more groups bonded to a silicon atom in a silyl group.

The term "alkoxy" refers to a monovalent group having an oxy group bonded directly to an alkyl group.

The term "aryloxy" refers to a monovalent group having an oxy group bonded directly to an aryl group.

The terms "aralkyloxy" and "alkaryloxy" refer to a monovalent group having an oxy group bonded directly to an aralkyl group or an alkaryl group, respectively.

The term "acyloxy" refers to a monovalent group of formula —O(CO)$R^b$ where $R^b$ is alkyl, aryl, aralkyl, or alkaryl. Suitable alkyl $R^b$ groups often have 1 to 10 carbon atoms, 1 to 6 carbon atoms, or 1 to 4 carbon atoms. Suitable aryl $R^b$ groups often have 6 to 12 carbon atoms such as, for example, phenyl. Suitable aralkyl and alkaryl $R^b$ groups often have an alkyl group with 1 to 10 carbon atoms, 1 to 6 carbon atoms, or 1 to 4 carbon atoms and an aryl having 6 to 12 carbon atoms.

The term "halo" refers to a halogen atom such as fluoro, bromo, iodo, or chloro. When part of a reactive silyl, the halo group is often chloro.

The term "(meth)acryloyloxy group" includes an acryloyloxy group (—O—(CO)—CH=CH$_2$) and a methacryloyloxy group (—O—(CO)—C(CH$_3$)=CH$_2$).

The term "(meth)acrylolyamino group" includes an acryloylamino group (—NR—(CO)—CH=CH$_2$) and a methacryloylamino group (—NR—(CO)—C(CH$_3$)=CH$_2$) including embodiments wherein the amide nitrogen is bonded to a hydrogen, methyl group, or ethyl group (R is H, methyl, or ethyl).

The term "brush copolymer" refers to a copolymer where at least one of the repeat units is derived from a macromonomer. Macromonomers are polymeric chains (typically, with at least 10 repeat units) that have a polymerizable group (e.g., an ethylenically unsaturated group) at one end.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list, refers to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

When a group is present more titan once in a formula described herein, each group is "independently" selected, whether specifically stated or not. For example, when more than one R group is present in a formula, each R group is independently selected. Furthermore, subgroups contained within these groups are also independently selected. For example, when each R group contains a Y group, each Y is also independently selected.

As used herein, the term "room temperature" refers to a temperature of 20° C. to 25° C. or 22° C. to 25° C.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF EXEMPLARY EMBODIMENTS

The present disclosure provides polyoxazoline (POx) copolymers.

In recent years, the use of polyoxazolines (POx) in biomedical applications has gained interest due to their high biocompatibility and stealth behavior that resembles PEG. POx's can be obtained through living cationic ring opening polymerization, which provides an easy access to a wide variety of well-defined polymers. Furthermore, the functionality and the resulting physical properties of POx's can be tuned simply by changing the initiator, monomer, and the end-group used in the polymerization. Poly(methyl-oxazoline)s and poly(ethyl-oxazoline)s have been shown to have faster in-vivo clearance and in the case of poly(methyl-oxazoline) more hydrophilic character than PEG, which can afford an advantage for nonfouling applications.

The present disclosure provides novel copolymers, and in certain embodiments, amphiphilic copolymers, where polyoxazolines are employed as the hydrophilic component and a perfluorinated group is employed as the hydrophobic component. Such polyoxazoline copolymers, particularly the amphiphilic copolymers, are useful in making coatings that resist biofilm formation, or enhance the release of formed biofilms.

In one embodiment, the present disclosure provides a copolymer derived from a monomer mixture that includes monomers of the formulas:

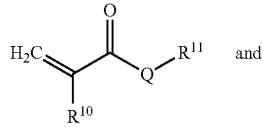
(A)

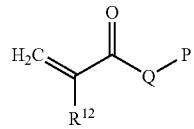
(B)

As used herein, a copolymer is a polymer containing two or more different monomeric (repeat) moieties (including terpolymers, tetrapolymers etc). Such copolymers can be random copolymers, block copolymers, or any other structural arrangement of monomeric moieties. In certain embodiments, such copolymers are brush copolymers.

Such copolymers of the present disclosure have a weight average molecular weight of at least 2,000 g/mol.

In certain embodiments, Q is O or N. In certain embodiments Q is O.

In certain embodiments, $R^{10}$ is H or $CH_3$. In certain embodiments, $R^{10}$ is H.

In certain embodiments, $R^{11}$ is an organic group that includes a hydrolyzable silyl group. In certain embodiments, $R^{11}$ is —Z—Si($R^{13}$)$_3$.

In certain embodiments, $R^{12}$ is H or $CH_3$. In certain embodiments, $R^{12}$ is H.

In certain embodiments, each $R^{13}$ group is independently a hydrolyzable group or a non-hydrolyzable group (e.g., an alkyl group, an aryl group, or a combination thereof (i.e., an alkaryl group or an aralkyl group)). In certain embodiments, each $R^{13}$ is independently selected from an alkyl group, an aryl group, a combination thereof, and a hydrolyzable group; and at least one $R^{13}$ is a hydrolyzable group. In certain embodiments, the hydrolyzable group is selected from a halo, an alkoxy group, and an acyloxy group. In certain embodiments, the hydrolyzable group is selected from a halo, a (C1-C4)alkoxy group, and a (C1-C4)acyloxy group.

In certain embodiments, Z is selected from an alkylene group, an arylene group, and a combination thereof (i.e., an alkarylene group or an aralkylene group), optionally including —O—, —C(O)—, —NR— (wherein R can be H, methyl, or ethyl, and is typically, H), —S—, or a combination thereof, within the chain, in this context, "within" means that such atoms or groups are not directly bonded to the silyl group or the —C(O)Q-group. In certain embodiments, Z is selected from a (C1-C20)alkylene group, a (C6-C12)arylene group, and a combination thereof, optionally including —O—, —C(O)—, —NR— (wherein R can be H, methyl, or ethyl, and is typically, H), —S—, or a combination thereof, within the chain.

In certain embodiments, P is (wherein (*) is the point of attachment to Q in Monomer B):

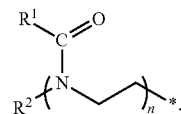

In certain embodiments, $R^1$ is selected from H, an alkyl group, an aryl group, and combinations thereof. In certain embodiments, $R^1$ is H, a (C1-C20)alkyl group, a (C6-C12) aryl group, a (C6-C12)ar(C1-C20)alkyl group, or a (C1-C20)alk(C6-C12)aryl group. In certain embodiments, $R^1$ is selected from H, methyl, and ethyl.

In certain embodiments, $R^2$ is selected from an alkyl group, an aryl group, and a $R^f$—Y—$(CH_2)_x$— group. In certain embodiments, $R^2$ is a $R^f$—Y—$(CH_2)_x$— group.

In certain embodiments, Y is selected from a bond, —S(O)$_2$—N(CH$_3$)—, —S(O)$_2$—N(CH$_2$CH$_3$)—, —S(O)$_2$—O—, —S(O)$_2$—, —C(O)—, —C(O)—S—, —C(O)—O—, —C(O)—NH—, —C(O)—N(CH$_3$)—, —C(O)—N(CH$_2$CH$_3$)—, —CH$_2$CH$_2$O)$_y$—, —O—, and —O—C(O)—CH=CH—C(O)—O—. In certain embodiments, Y is selected from a bond, —S(O)$_2$—N(CH$_3$)—, —C(O)—NH—, and —(CH$_2$CH$_2$O)$_y$—.

In certain embodiments, $R^f$ is a perfluorinated alkyl group. In certain embodiments, $R^f$ is a perfluorinated (C1-C8)alkyl group. In certain embodiments, $R^f$ is a perfluorinated (C1-C5)alkyl group or a perfluorinated (C1-C4)alkyl group, in certain embodiments, $R^f$ is a perfluorinated C4 alkyl group.

In certain embodiments, n is an integer of greater than 2. In certain embodiments, n is greater than 10. In certain embodiments, n is at least 20. In certain embodiments, n is no greater than 500. In certain embodiments, n is no greater than 100. In certain embodiments, n is 20 to 100.

In certain embodiments, x is an integer of at least 2. In certain embodiments, x is no greater than 20. In certain embodiments x is no greater than 10. In certain embodiments, x is no greater than 6.

In certain embodiments, y is an integer of at least 1. In certain embodiments, y is no greater than 20. In certain embodiments, y is no greater than 5.

In one embodiment, the present disclosure provides a copolymer derived from monomers having the formulas:

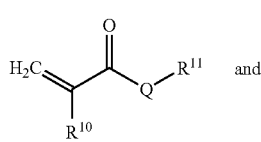
(A)

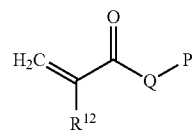
(B)

wherein: Q is O or N; $R^{10}$ is H or $CH_3$; $R^{11}$ is an organic group that includes a hydrolyzable silyl group; $R^{12}$ is H or $CH_3$; P is (wherein (*) is the point of attachment, to Q in Monomer B):

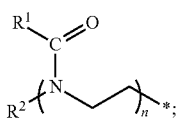

R[1] is selected from H, an alkyl group, an aryl group, and a combination thereof; R[2] is selected from an alkyl group, an aryl group, and a R[f]—Y—(CH$_2$)$_x$— group; R[f] is a perfluorinated alkyl group; Y is selected from a bond, —S(O)$_2$—N(CH$_3$)—, —S(O)$_2$—N(CH$_2$CH$_3$)—, —S(O)$_2$—O—, —S(O)$_2$—, —C(O)—, —C(O)—S—, —C(O)—O—, —C(O)—NH—, —C(O)—N(CH$_3$)—, —C(O)—N(CH$_2$CH$_3$)—, —(CH$_2$CH$_2$O)$_y$—, —O—, and —O—C(O)—CH═CH—C(O)—O—; n is an integer of greater than 2; x is an integer of at least 2; and y is an integer of at least 1.

In certain embodiments, examples of Monomer A include the following:

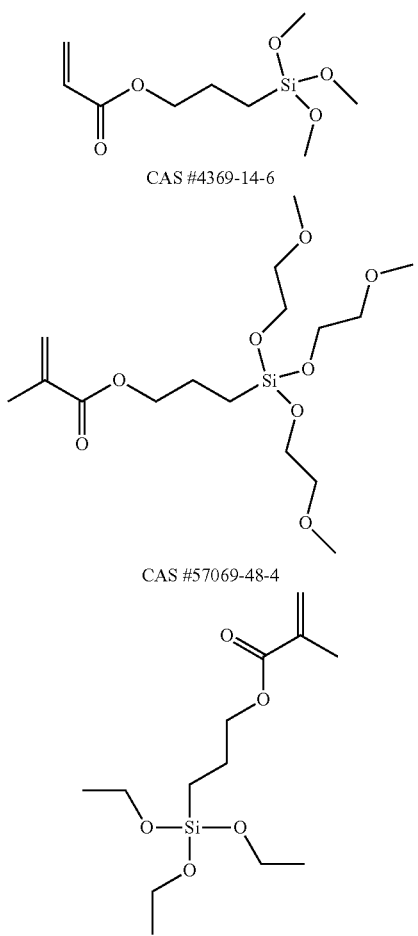

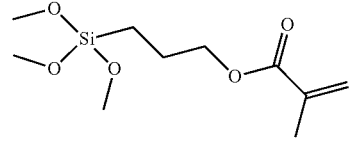

CAS #2530-85-0

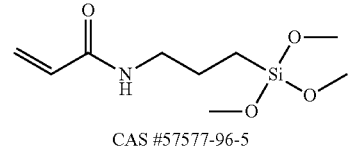

CAS #57577-96-5

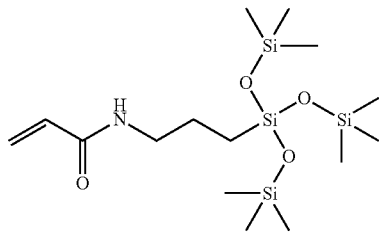

CAS #115258-10-1

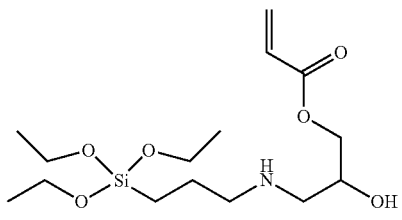

CAS #123198-57-2

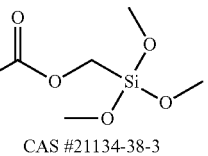

CAS #21134-38-3

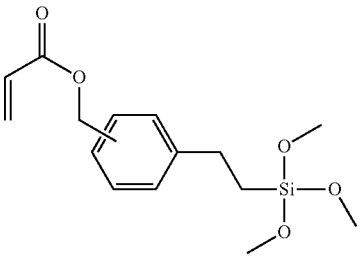

CAS #141813-19-6

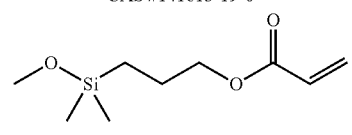

CAS #111918-90-2

In certain embodiments, Monomer B is of the formula:

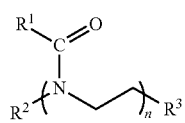

wherein: R[1] is selected from H, an alkyl group, an aryl group, and combinations thereof; R[2] is R[f]—Y—(CH$_2$)$_x$—;

R³ is a (meth)acryloyloxy group or a (meth)acryloylamino group; R^f is a perfluorinated alkyl group; Y is selected from a bond, —S(O)₂—N(CH₃)—, —S(O)₂—N(CH₂CH₃)—, —S(O)₂—O—, —S(O)₂—, —C(O)—, —C(O)—S—, —C(O)—O—, —C(O)—NH—, —C(O)—N(CH₃)—, —C(O)—N(CH₂CH₃)—, —(CH₂CH₂O)_y—, —O—, and —O—C(O)—CH=CH—C(O)—O—; n is an integer of greater than 10; x is an integer from 2 to 20; and y is an integer of at least 1.

Monomer B is a polymerizable polyoxazoline. Examples of Monomer B include:

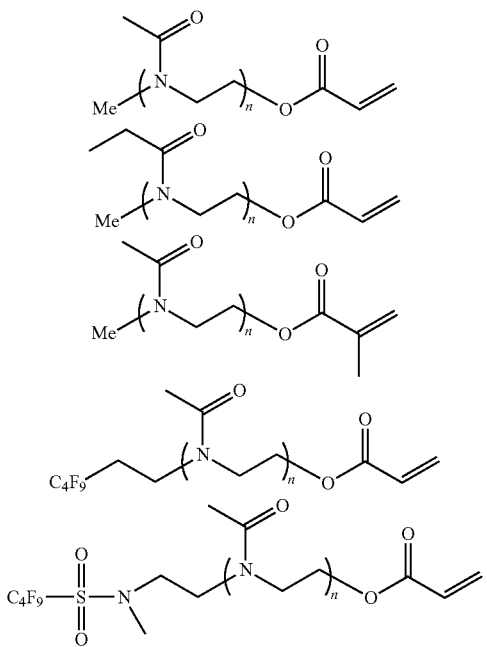

In some more specific examples, n in these formulas are in a range of 20 to 40, in a range of 25 to 35, or equal to 30.

Such compounds can be made using conventional techniques. An exemplary reaction scheme is shown in the Examples Section (Scheme I). Typically, an oxazoline, particularly a 2-oxazoline that includes an R¹ group at the 2-position, is subjected to a ring opening reaction in a suitable solvent (e.g., acetonitrile) in the presence of an initiator (e.g., methyl trifluoromethansulfonate (i.e., methyl triflate), perfluorobutyl ethylene triflate, perfluorobutyl sulfonamide triflate, methyl toluene sulfonate (i.e., methyl tosylate), and methyl iodide) with heating (e.g., at a temperature of 80° C.), and subsequently modified to include a polymerizable group (e.g., upon reaction with (meth)acrylic acid in the presence of a base (e.g., triethylamine)).

In one embodiment, the present disclosure provides a brush copolymer derived from a monomer mixture that includes monomers having the formulas:

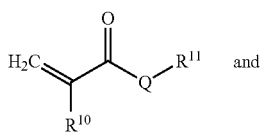

(A)

and

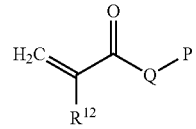

(B)

wherein: Q is O or N; R¹⁰ is H or CH₃; R¹¹ is —Z—Si(R¹³)₃; R¹² is H or CH₃; each R¹³ is independently selected from an alkyl group, an aryl group, or a combination thereof, and a hydrolyzable group; at least one R¹³ is a hydrolyzable group; Z is selected from an alkylene group, an arylene group, and a combination thereof, optionally including —O—, —C(O)—, —NH—, —S—, or a combination thereof, within the chain; P is (wherein (*) is the point of attachment to Q in Monomer B):

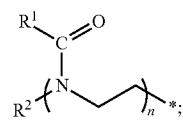

wherein: R¹ is selected from H, an alkyl group, an aryl group, and combinations thereof; R² is R^f—Y—(CH₂)_x— group; R^f is a perfluorinated (C1-C8)alkyl group; Y is a bond, —S(O)₂—N(CH₃)—, —C(O)—O—, —C(O)—NH—, or —(CH₂CH₂O)_y—, n is an integer from 20 to 100; x is an integer from 2 to 20; and y is an integer from 1 to 20.

Monomer A has a hydrolyzable silyl group that can be used to crosslink the copolymer, to attach the copolymer to a substrate, or both. That is, the hydrolyzable silyl group undergoes a hydrolysis and/or condensation reaction that results in the formation of one or more silicon-oxygen-silicon linkages. Crosslinks within the copolymer can result when two hydrolyzable silyl groups react with each other. Substrate attachment can result when a hydrolyzable silyl group reacts with a silanol group on a substrate.

In making the copolymer of the disclosure, the amount of Monomer A typically used is at least 1 weight percent (wt-%), or at least 5 wt-%, or at least 10 wt-%, based on the total amount of monomers. In making the copolymer of the disclosure, the amount of Monomer A typically used is no more than 50 wt-%, based on the total amount of monomers. The balance (50-99 wt-%) often includes Monomer B, although Monomers A and B can also be copolymerized with other monomers, such as other ethylenically unsaturated monomers to make suitable coatings. Some example optional monomers include various alkyl acrylates, alkyl methacrylates, aryl acrylates, aryl methacrylates, vinyl ethers, vinyl esters, and styrene. If used, these additional monomers can be present in any desired amounts such as, for example, in amounts up to 10 wt-%, up to 20 wt-%, or up to 30 wt-% of the total amount of monomers.

Monomer A and Monomer B are copolymerized using a free radical polymerization reaction. That is, Monomer A and Monomer B are typically combined with a free radical initiator and subjected to conditions suitable for polymerization. The free radical initiator can be a thermal initiator or a photoinitiator. The initiator is typically present in an amount in the range of 0.01 to 5 weight percent, in the range of 0.01 to 2 weight percent, in the range of 0.01 to 1 weight percent, or in the range of 0.01 to 0.5 weight percent based on a total weight of polymerizable material (e.g., Monomer A, Monomer B, and any optional monomers) in the polymerizable mixture.

In some embodiments, a thermal initiator is used. Thermal initiators can be water-soluble or water-insoluble (i.e., oil-soluble) depending on the particular polymerization method used. Suitable water-soluble initiators include, but are not limited to, persulfates such as potassium persulfate, ammonium persulfate, sodium persulfate, and mixtures thereof; an oxidation-reduction initiator such as the reaction product of a persulfate and a reducing agent such as a metabisulfite (e.g., sodium metabisulfite) or a bisulfate (e.g., sodium bisulfate); or 4,4'-azobis(4-cyanopentanoic acid) and its soluble salts (e.g., sodium or potassium). Suitable oil-soluble initiators include, but are not limited to, various azo compound such as those commercially available under the trade designation VAZO from E. I. DuPont de Nemours Co. including VAZO 67, which is 2,2'-azobis(2-methylbutane nitrile), VAZO 64, which is 2,2'-azobis(isobutyronitrile), and VAZO 52, which is (2,2'-azobis(2,4-dimethylpentanenitrile); and various peroxides such as benzoyl peroxide, cyclohexane peroxide, lauroyl peroxide, and mixtures thereof.

In many embodiments, a photo initiator is used. Some exemplary photoinitiators are benzoin ethers (e.g., benzoin methyl ether or benzoin isopropyl ether) or substituted benzoin ethers (e:g., anisoin methyl ether), Other exemplary photoinitiators are substituted acetophenones such as 2,2-diethoxyacetophenone or 2,2-dimethoxy-2-phenylacetophenone (commercially available under the trade designation IRGACURE 651 from BASF Corp. (Florham Park, N.J., USA) or under the trade designation ESACURE KB-1 from Sartomer (Exton, Pa., USA)). Still other exemplary photoinitiators are substituted alpha-ketols such as 2-methyl-2-hydroxypropiophenone, aromatic sulfonyl chlorides such as 2-naphthalenesulfonyl chloride, and photoactive oximes such as 1-phenyl-1,2-propanedione-2-(O-ethoxycarbonyl) oxime. Other suitable photoinitiators include, for example, 1-hydroxycyclohexyl phenyl ketone (IRGACURE 184), bis(2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The polymerizable mixture may optionally further contain a chain transfer agent to control the molecular weight of the resultant elastomeric material. Examples of useful chain transfer agents include, but are not limited to, carbon tetrabromide, alcohols, mercaptans such as isooctylthioglycolate, and mixtures thereof. If used, the polymerizable mixture may include up to 0.5 weight of a chain transfer agent based on a total weight of polymerizable material. For example, the polymerizable mixture can contain 0.01 to 0.5 weight percent, 0.05 to 0.5 weight percent, or 0.05 to 0.2 weight percent chain transfer agent.

If desired, copolymers of the present disclosure can be combined with components such as metal silicates (e.g., lithium silicate) to form hard coatings, as is known in the art.

Such polyoxazoline copolymers are useful in making biofilm-resistant coatings (i.e., coatings that resist biofilm formation and/or enhance the release of formed biofilms, as evidenced by resistance to the growth of at least one microorganism). Thus, methods of coating a substrate to improve biofilm resistance of the substrate (relative to the uncoated substrate) are provided by the present disclosure.

In one embodiment, a coating composition is provided that includes a polyoxazoline copolymer of the present disclosure and a solvent, whereby the coating compositions are applied to substrates to impart a biofilm-resistant coating thereto. The coating composition often includes a copolymer with pendant hydrolyzable silyl groups. That is, the copolymer in the coating composition is not crosslinked (e.g., cured). In another embodiment, there is a method for coating a substrate, particularly a hard substrate, with a coating composition of the present disclosure to provide a biofilm-resistant coating thereto. A wide variety of coating methods can be used to apply a composition of the present disclosure, such as brushing, spraying, dipping, rolling, spreading, and the like. The obtained coating on the substrate may be cured at room temperature or at art elevated temperature (e.g., 40° C. to 300° C.). In some embodiments the curing may be effected by a catalyst, at room or elevated temperatures. Curing often involves reaction of the pendant hydrolyzable silyl groups to form a crosslinking containing a —Si—O—Si— linkage group.

Useful solvents for the coating compositions include any that do not deleteriously affect polymerization of the monomers (if the coating solvent is the same as used in the polymerization process) and in which the components are soluble to at least 1% by weight. Examples of solvents are water, methanol, ethanol, isopropanol, acetone, methyl ethyl ketone, methyl iso-butyl ketone, methyl acetate, ethyl acetate, heptane, toluene, xylene, and ethylene glycol alkyl ether. Those solvents can be used alone or as mixtures thereof. If the copolymer contains pendent hydrolyzable silyl groups, preferably the solvent component contains an alcohol solvent which tends to temporarily retard the reaction between these groups.

The coating composition is typically a homogeneous mixture that has a viscosity appropriate to the application conditions and method. For example, a material to be brush or roller coated would likely be preferred to have a higher viscosity than a dip coating solution. The coating composition is typically a relatively dilute solution, often containing at least 0.1 wt-%, or at least 1 wt-%, of the copolymer. A typical coating composition often contains no more than 50 wt-%, or no more than 25 wt-%, of the copolymer.

The substrate on which the coating can be disposed for the formation of a biofilm-resistant coating can be any of a wide variety of materials. Useful substrates include ceramics, siliceous substrates including glass, metal, natural and man-made stone, woven and nonwoven articles, polymeric materials, including thermoplastics and thermosets, including, for example, poly(meth)acrylates, polycarbonates, polystyrenes, styrene copolymers such as styrene acrylonitriie copolymers, polyesters, polyethylene terephthalate, silicones such as that used in medical tubing, paints such as those based on acrylic resins, powder coatings such as polyurethane or hybrid powder coatings, and wood. The substrate can be in the form of a film, woven, or nonwoven, for example.

In some embodiments, the substrate is selected to have a group that can react with the polyoxazoline copolymers of the present disclosure. For example, the substrate can have a glass or ceramic-containing surface that has silanol groups that can undergo a condensation reaction with group R selected from a trialkoxysilylalkyl group. The product of this reaction results in the formation of a —Si—O—Si— bond between the polyoxazoline and the substrate.

Various articles can be effectively treated with the coating composition of the present invention to provide a biofilm-resistant coating thereon. The present invention also provides a coated article, such as a film. Thus, the present disclosure provides an article comprising a substrate (e.g., a film), wherein the substrate includes at least one surface having a layer that includes a copolymer of the present disclosure disposed thereon.

Preferably, the substrate to which coating is to be applied should be clean prior to application to obtain optimum characteristic and durability. Metallic as well as glass surfaces are often covered with organic contaminants. Before the coatings of the invention can be applied to such surfaces, they should he cleaned by at least solvent wiping. In the case of gross contamination, the metallic or glass surface may have to be etched, anodized, or treated in ways known to those skilled in the art. For example, if the surface of steel is coated with rust, that rust may have to be etched away by an acid treatment. Once the surface of the metal is exposed, the coating can be applied.

Biofilms typically develop where the substrate is in contact with water or exposed to humid conditions. The coatings of the present disclosure retard the formation of such biofilms, particularly when exposed to circulating water. It is believed that the microorganisms are unable of minimally able to attach to the coated surfaces. Further, it is believed that extant biofilms are more easily removed from the coated surface. Thus, the curable composition is particularly suited for substrates in wet or humid environments such as in medical catheter coatings, antifouling marine coatings, coatings for water handling equipment, heat exchangers and other HVAC equipment, coatings for filter media, and dental equipment, devices and materials that may be used in the oral cavity.

Illustrative embodiments of the present disclosure are listed below.

Embodiment 1 is a copolymer derived from a monomer mixture comprising monomers having the formulas:

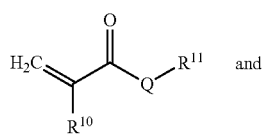

(A)

and

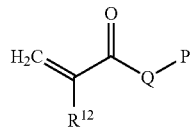

(B)

wherein:
Q is O or N;
$R^{10}$ is H or $CH_3$;
$R^{11}$ is an organic group comprising a hydrolyzable silyl group;
$R^{12}$ is H or $CH_3$; and
P is:

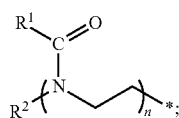

wherein:
$R^1$ is selected from H, an alkyl group, an aryl group, and a combination thereof;
$R^2$ is selected from an alkyl group, an aryl group, a combination thereof, and a $R^f$—Y—$(CH_2)_x$— group;
$R^f$ is a perfluorinated alkyl group;
Y is selected from a bond, —$S(O)_2$—$N(CH_3)$—, —$S(O)_2$—$N(CH_2CH_3)$—, —$S(O)_2$—O—, —$S(O)_2$—, —C(O)—, —C(O)—S—, —C(O)—O, —C(O)—NH—, —C(O)—$N(CH_3)$—, —C(O)—$N(CH_2CH_3)$—, —$(CH_2CH_2O)_y$—, —O—, and —O—C(O)—CH═CH—C(O)—O—;
n is an integer of greater than 2;
x is an integer of at least 2; and
y is an integer of at least 1.

Embodiment 2 is the copolymer of embodiment 1, wherein the copolymer is a random or block copolymer.

Embodiment 3 is the copolymer of embodiment 1 or 2 which is a brush copolymer.

Embodiment 4 is the copolymer of any one of embodiments 1 through 3 which has a weight average molecular weight of at least 2,000 g/mol.

Embodiment 5 is the copolymer of any one of embodiments 1 through 4 wherein $R^{11}$ is —Z—$Si(R^{13})_3$ wherein:
each $R^{13}$ is independently selected from an alkyl group, an aryl group, a combination thereof, and a hydrolyzable group;
at least one $R^{13}$ is a hydrolyzable group; and
Z is selected from an alkylene group, an arylene group, and a combination thereof, optionally including —O—, —C(O)—, —NH—, —S—, or a combination thereof, within the chain.

Embodiment 6 is the copolymer of embodiment 5 wherein the hydrolyzable group is selected from a halo, a (C1-C4) alkoxy group, and a (C1-C4)acyloxy group.

Embodiment 7 is the copolymer of embodiment 5 or 6 wherein Z is selected from a (C1-C20)alkylene group, an (C6-C12)arylene group, and a combination thereof, optionally including —O—, C(O)—, —NH—, —S—, or a combination thereof, within the chain.

Embodiment 8 is the copolymer of any one of embodiments 1 through 7 wherein $R^1$ is selected from H, methyl, and ethyl.

Embodiment 9 is the copolymer of any one of embodiments 1 through 8 wherein $R^2$ is a $R^f$—Y—$(CH_2)_x$-group.

Embodiment 10 is the copolymer of any one of embodiments 1 through 9 wherein Y is selected from a bond, —$S(O)_2$—$N(CH_3)$—, —C(O)—NH—, and —$(CH_2CH_2O)_y$—.

Embodiment 11 is the copolymer of any one of embodiments 1 through 10 wherein $R^f$ is a perfluorinated (C1-C8) alkyl group.

Embodiment 12 is the copolymer of any one of embodiment 11 wherein $R^f$ is a perfluorinated (C1-C5)alkyl group.

Embodiment 13 is the copolymer of embodiment 12 wherein $R^f$ is a perfluorinated C4 alkyl group.

Embodiment 14 is the copolymer of any one of embodiments 1 through 13 wherein n is an integer of no greater than 500.

Embodiment 15 is the copolymer of embodiment 14 wherein n is an integer of greater than 10.

Embodiment 16 is the copolymer of embodiment 15 wherein n is an integer from 20 to 100.

Embodiment 17 is the copolymer of any one of embodiments 1 through 16 wherein x is an integer of no greater than 20.

Embodiment 18 is the copolymer of any one of embodiments 1 through 17 wherein x is an integer from 2 to 10.

Embodiment 19 is the copolymer of embodiment 18 wherein x is an integer from 2 to 6.

Embodiment 20 is the copolymer of any one of embodiments 1 through 19 wherein y is an integer of no greater than 20.

Embodiment 21 is the copolymer of embodiment 20 wherein y is an integer from 1 to 5.

Embodiment 22 is the copolymer of any one of embodiments 1 through 21 derived from at least 1 wt-% of monomer A.

Embodiment 23 is the copolymer of embodiment 22 derived from at least 5 wt-% of monomer A.

Embodiment 24 is the copolymer of embodiment 23 derived from at least 10 wt-% of monomer A.

Embodiment 25 is the copolymer of any one of embodiments 1 through 24 derived from no more than 50 wt-% of monomer A.

Embodiment 26 is the copolymer of any one of embodiments 1 through 25 wherein monomer B is of the formula:

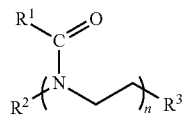

wherein;
$R^1$ is selected from H, an alkyl group, an aryl group, and combinations thereof;
$R^2$ is $R^f$—Y—$(CH_2)_x$—;
$R^3$ is a (meth)acryloyloxy group or a (meth)acryloylamino group;
$R^f$ is a perfluorinated alkyl group;
Y is selected from a bond, —S(O)$_2$—N(CH$_3$)—, —S(O)$_2$—N(CH$_2$CH$_3$)—, —S(O)$_2$—O—, —S(O)$_2$—, —C(O)—, —(O)—S—, —C(O)—O—, —C(O)—NH—, —C(O)—N(CH$_3$)—, —C(O)—N(CH$_2$CH$_3$)—, —(CH$_2$CH$_2$O)$_y$—, —O—, and —O—C(O)—CH=CH—C(O)—O—;
n is an integer of greater than 10;
x is an integer from 2 to 20; and
y is an integer from at least 1.

Embodiment 27 is a brush copolymer derived from a monomer mixture comprising monomers having, the formulas:

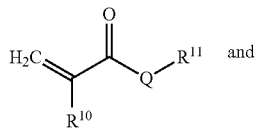

(A)

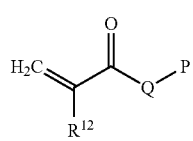

(B)

wherein:
Q is O or N;
$R^{10}$ is H or CH$_3$;
$R^{11}$ is —Z—Si(R$^{13}$)$_3$;
$R^{12}$ is H or CH$_3$;
each $R^{13}$ is independently selected from an alkyl group, an aryl group, a combination thereof, and a hydrolyzable group;
at least one $R^{13}$ is a hydrolyzable group;
Z is selected from an alkylene group, an arylene group, and a combination thereof, optionally including —O—, —C(O)—, —NH—, —S—, or a combination thereof, within the chain; and
P is:

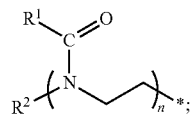

wherein;
$R^1$ is selected from H an alkyl group, an aryl group, and combinations thereof;
$R^2$ is $R^f$—Y—$(CH_2)_x$— group;
$R^f$ is a perfluorinated (C1-C8)alkyl group;
Y is a bond, —S(O)$_2$—N(CH$_3$)—, —C(O)—O—, —C(O)—NH—, or —(CH$_2$CH$_2$O)$_y$—;
n is an integer from 20 to 100;
x is an integer from 2 to 20; and
y is an integer from 1 to 20.

Embodiment 28 is a composition comprising a copolymer of any one of embodiments 1 through 27 and a solvent.

Embodiment 29 is a method of coating a substrate to improve biofilm resistance of the substrate, the method comprising coating at least one surface of the substrate with the composition of embodiment 28.

Embodiment 30 is an article comprising a substrate, wherein the substrate comprises at least one surface having a layer comprising a copolymer of any one of embodiments 1 through 27 disposed thereon.

Embodiment 31 is the article of claim 30 wherein the substrate is in the form of a film.

EXAMPLES

Objects and advantages of this disclosure are further illustrated by the following examples, but the particular materials and amounts thereof recited in these examples, as well as other conditions and details, should not be construed to unduly limit this disclosure.

General Procedures for Polymer Synthesis:

Glassware was dried overnight in an oven at 150° C. prior to use. Reagents were purchased from Fisher Scientific or Sigma Aldrich. Acetonitrile was anhydrous grade. Methyl iodide, methyl tosylate, and oxazoline monomers were distilled over CaH$_2$ and stored over 3 Å molecular sieves. Other reagents for oxazoline polymerization were stored over 3 Å molecular sieves prior to use. Solvents were removed at reduced pressure using a rotary evaporator.

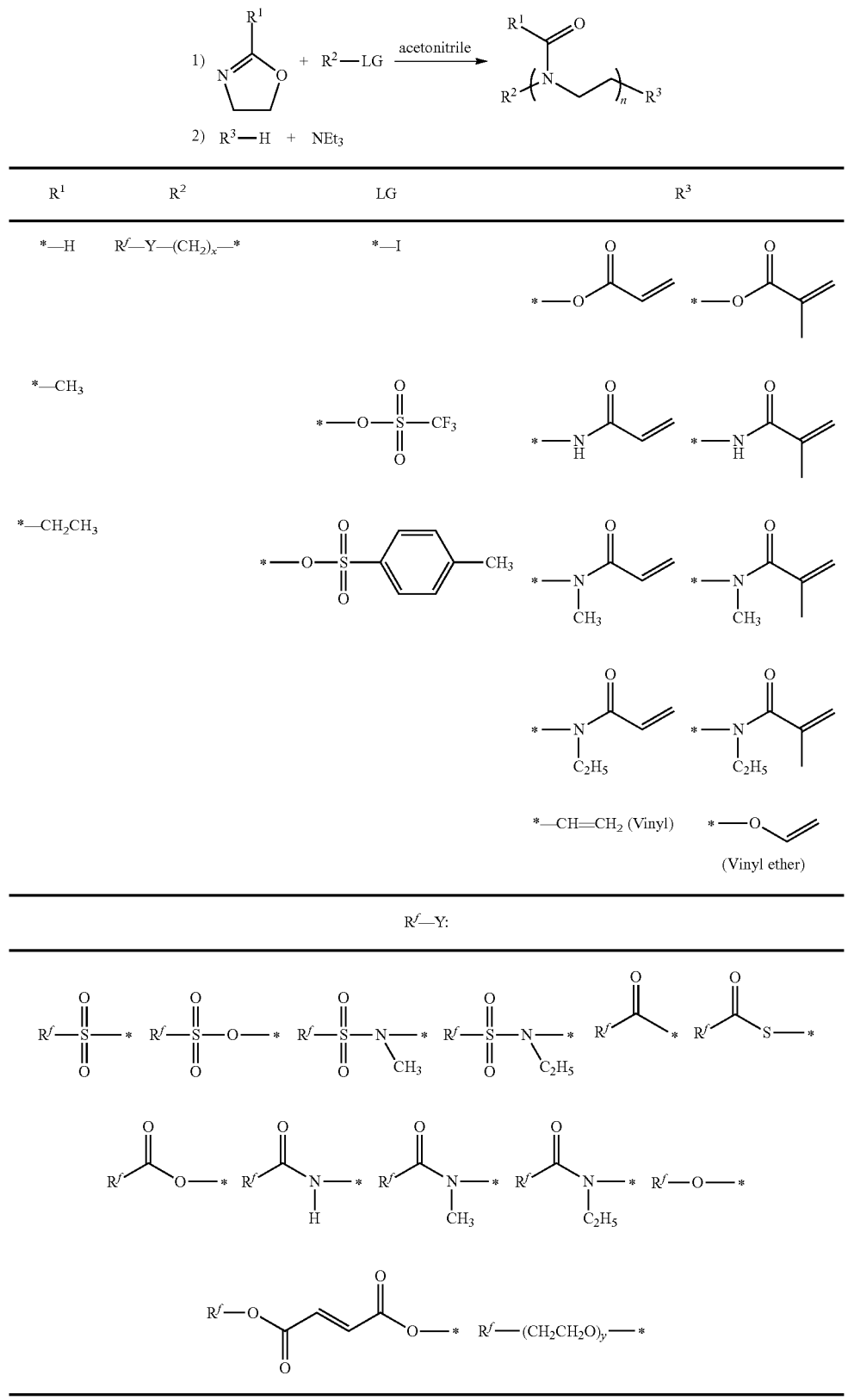
Scheme I: General scheme for the synthesis of poly(oxazoline) polymers (wherein "LG" = leaving group, and the * represents the point of attachment of the group)

Preparatory Example 1

Synthesis of Polymerizable Polyoxazoline (Monomer B)

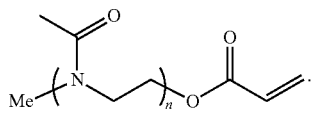

A 3-necked flask with attached condenser and stopcock was purged with nitrogen, then charged with acetonitrile (15 mL) and methyl p-toluenesulfonate (0.73 g, 3.9 mmol). The solution was cooled to 0° C., then 2-methyl-2-oxazoline (10.0 g, 117 mmol) was added by syringe. After stirring for 2 hours while slowly warming to room temperature, the solution was heated to 80° C. in an oil bath, then stirred for 20 hours. After cooling to room temperature, acrylic acid (0.42 g, 5.9 mmol) and triethylamine (0.79 g, 7.8 mmol) were added by syringe in that order. The solution was heated back up to 80° C., and stirred for another 24 hours. After cooling, the solution was filtered, then added dropwise with vigorous stirring to 200 mL of diethyl ether to precipitate the polymer. The resulting suspension was stirred for 2 days. The precipitate was isolated by filtration, washed with diethyl ether, and dried under vacuum at 80° C. overnight, yielding 11 g of white solid. Accounting for the presence of triethylammonium tosylate impurities, the yield was close to quantitative. End-group analysis by $^1$H-NMR spectroscopy showed that polymer with n=30 was obtained.

Preparatory Example 2

Synthesis of Polymerizable Polyoxazoline (Monomer B)

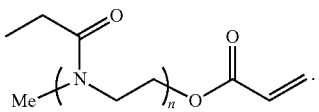

A 3-necked flask with attached condenser and stopcock was purged with nitrogen, then charged with acetonitrile (15 mL) and methyl trifluoromethanesulfonate (0.165 g, 1.01 mmol). The solution was cooled to 0° C., then 2-ethyl-2-oxazoline (3.0 g, 30.2 mmol) was added by syringe. After stirring for 2 hours while slowly warming to room temperature, the solution was heated to 80° C. in an oil bath, then stirred for 20 hours. After cooling to room temperature, acrylic acid (0.37 g, 5.1 mmol) and triethylamine (0.6 g, 6.06 mmol) were added by syringe in that order. The solution was heated back up to 80° C., and stirred for another 24 hours. After cooling, the solution was filtered, then added dropwise with vigorous stirring to 200 mL of cold diethyl ether to precipitate the polymer. The resulting suspension was stirred for 15 min. The precipitate was isolated by filtration, washed with diethyl ether, and dried under vacuum at 80° C. overnight, yielding 2.9 g of white solid. End-group analysis by $^1$H-NMR spectroscopy showed that polymer with n=30 was obtained.

Preparatory Example 3

Synthesis of Polymerizable Polyoxazoline (Monomer B)

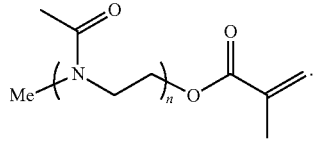

A 3-necked flask with attached condenser and stopcock was purged with nitrogen, then charged with acetonitrile (30 mL) and methyl trifluoromethanesulfonate (0.39 g, 2.3 mmol). The solution was cooled to 0° C., then 2-methyl-2-oxazoline (6.0 g, 70.6 mmol) was added by syringe. After stirring for 2 hours while slowly warming to room temperature, the solution was heated to 80° C. in an oil bath, then stirred for 20 hours. The solution was cooled to 0° C. and saturated 20 ml of Na$_2$CO$_3$ was added. The resulting mixture was heated to 80° C. in an oil bath, then stirred for 12 hours. The solvent was removed under vacuum and the polymer was extracted with dichloromethane from the solute. The excess dichloromethane was removed under vacuum to yield 5.9 g of white solid. End-group analysis by $^1$H-NMR spectroscopy showed that polymer with n=30 was obtained.

For the next step, 5.0 g of the hydroxyl terminated poly(2-methyl-2-oxazoline)polymer was dissolved in 50 ml of anhydrous acetonitrile in a 3-necked flask with attached condenser and stopcock purged with nitrogen. The solution was cooled to 0° C., then methacryloyl chloride (0.42 g, 4.0 mmol) and triethylamine (0.5 g, 5.0 mmol) were added by syringe in that order. The solution was slowly warmed up to room temperature, and then stirred for additional 20 hours. The final polymer was added dropwise with vigorous stirring to 200 mL of cold diethyl ether to precipitate the polymer. The resulting suspension was stirred for 15 min. The precipitate was isolated by filtration, washed with diethyl ether, and dried under vacuum at 80° C. overnight, yielding 4.8 g of white solid.

Preparatory Example 4

Synthesis of R$^2$-LG

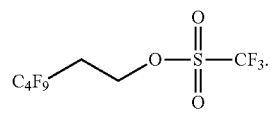

A round bottom flask, equipped with a stopcock, was purged with nitrogen, then charged with anhydrous dichloromethane (20 milliliters (mL)), 1,4-dioxane (20 mL), pyridine (2.0 grams (g), 24.6 millimoles (mmol)) and 1H, 1H, 2H, 2H-perfluorohexanol (5.0 g, 18.9 mmol). The solution was cooled to 0° C., then trifluoromethanesulfonic anhydride (7.0 g, 24.6 mmol) was added drop-wise by syringe to the vigorously stirring solution. After stirring for 2 hours at 0° C., the solution was slowly warmed to room temperature and then stirred for additional 10 hours. The resulting suspension was filtered to remove the precipitated salts. The solution was then successively washed with 1 Normal (N)

HCl, saturated NaHCO$_3$, 10% copper sulfide solution, and brine. The organic phase was dried over anhydrous Na$_2$SO$_4$ and excess solvent was removed under vacuum. The resulting brown oil was distilled under reduced pressure to yield 3.0 g of the product as colorless liquid.

Preparatory Example 5

Synthesis of Polymerizable Polyoxazoline (Monomer B)

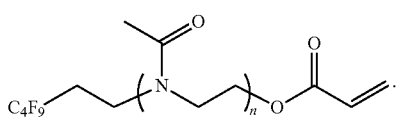

A 3-necked flask with attached condenser and stopcock was purged with nitrogen, then charged with acetonitrile (20 mL) and perfluorobutyl ethylene triflate (R$^2$-LG) initiator from Preparatory Example 4 (0.4 g, 1.0 mmol). The solution was cooled to 0° C., then 2-methyl-2-oxazoline (2.6 g, 30 mmol) was added by syringe. After stirring for 2 hours while slowly warming to room temperature, the solution was heated to 80° C. in an oil bath, then stirred for 20 hours. After cooling to room temperature, acrylic acid (0.36 g, 5.0 mmol) and triethylamine (0.61 g. 6.0 mmol) were added by syringe in that order. The solution was heated back up to 80° C., and stirred for another 24 hours. After cooling, the solution was filtered, then added dropwise with vigorous stirring to 200 mL of diethyl ether to precipitate the polymer. The resulting suspension was stirred for 15 min. The precipitate was isolated by filtration, washed with diethyl ether, and dried under vacuum at 80° C. overnight, yielding 2.6 g of white solid. End-group analysis by $^1$H-NMR spectroscopy showed that polymer with n=30 was obtained.

Preparatory Example 6

Synthesis of R$^2$-LG

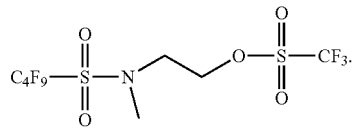

A round bottom flask, equipped with a stopcock, was purged with nitrogen, then charged with anhydrous dichloromethane (50 mL), 1,4-dioxane (50 mL), pyridine (3.6 g, 45.4 mmol) and N-methyl-1,1,2,2,3,3,4,4-nonafluoro-N-(2-hydroxyethyl)butane-1-sulphonamide (12.5 g, 34.9 mmol). The solution was cooled to 0° C., then trifluoromethanesulfonic anhydride (12.8 g, 45.4 mmol) was added drop-wise by syringe to the vigorously stirring solution. After stirring for 2 hours at 0° C., the solution was slowly warmed to room temperature and then stirred for 10 additional hours. The resulting suspension was filtered to remove the precipitated salts. The solution was then successively washed with 1N HCl, saturated NaHCO$_3$, 10% copper sulfide solution, and brine. The organic phase was dried over anhydrous Na$_2$SO$_4$ and excess solvent was removed under vacuum. Recrystallization of the resulting solid from cold toluene yielded 7.5 g of the product as white solid.

Preparatory Example 7

Synthesis of Polymerizable Polyoxazoline (Monomer B)

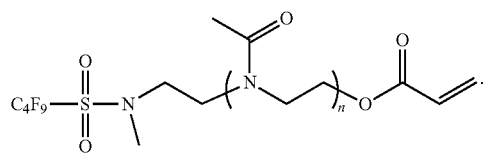

A 3-necked flask with attached condenser and stopcock was purged with nitrogen, then charged with acetonitrile (15 mL) and perfluorobutyl sulfonamide triflate (R$^2$-LG) initiator from Preparatory Example 6 (0.74 g, 1.5 mmol). The solution was cooled to 0° C., then 2-methyl-2-oxazoline (3.9 g, 46 mmol) was added by syringe. After stirring for 15 minutes, the solution was warmed to 80° C., then stirred for 16 hours. After cooling to room temperature, acrylic acid (0.16 g, 2.3 mmol) and triethylamine (0.31 g, 3.0 mmol) were added by syringe in that order. The solution was heated back up to 80 ° C., and stirred for another 4 hours. After cooling, the acetonitrile was evaporated with a stream of nitrogen, and the remainder was dissolved in 50 mL of chloroform. This solution was filtered, then concentrated to about 20 mL. The solution was then added dropwise, with vigorous stirring, to 200 mL of diethyl ether to precipitate the polymer. The resulting suspension was left in the freezer overnight. The precipitate was isolated by filtration, washed with diethyl ether, and dried under vacuum at 80° C. overnight, yielding 4.7 g of white solid. Accounting for the presence of triethylammonium triflate impurities, the yield was 96%. End-group analysis by $^1$H-NMR spectroscopy showed that polymer with n=30 was obtained.

Preparatory Example 8

Synthesis of Polymerizable Polyethylene Glycol

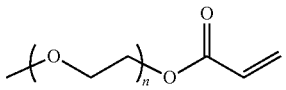

A round bottom flask, equipped with a stopcock, was purged with nitrogen, then charged with anhydrous dichloromethane (150 mL), triethylamine (5.3 g, 52.7 mmol), and poly(ethylene glycol)methyl ether (Mn~2000 g/mol) (20.0 g, 10.5 mmol). The solution was cooled to 0° C., then acryloyl chloride (4.8 g, 52.7 mmol) was added drop-wise by syringe to the vigorously stirring solution. After stirring for 2 hours at 0° C., the solution was slowly warmed to room temperature and then stirred for 10 additional hours. The solution was then successively washed with brine (3×200 ml). The organic phase was dried over anhydrous Na$_2$SO$_4$ and excess solvent was removed under vacuum. Recrystallization of the resulting solid from cold anhydrous diethyl ether yielded 17.5 g of the product as white solid.

Scheme II: General Synthesis of Brush Copolymers

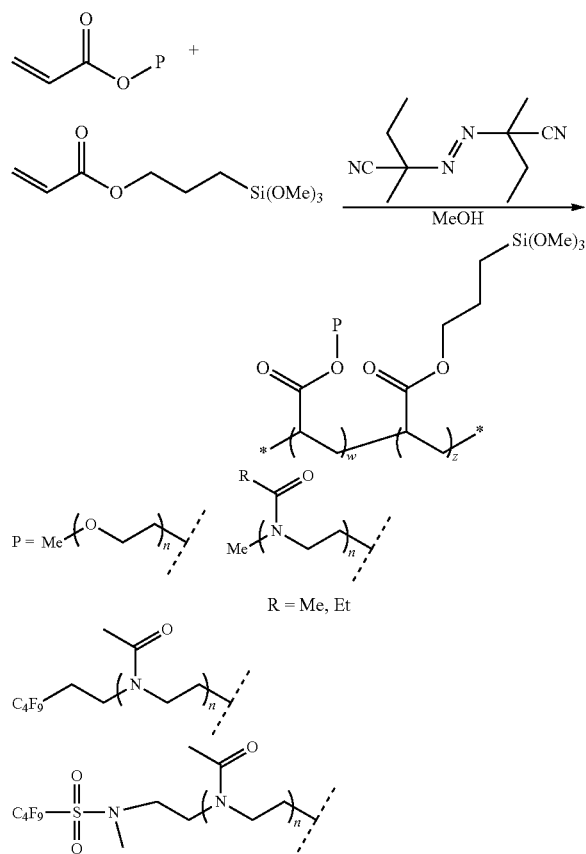

Comparative Example 1

Synthesis of PEG-Si Brash Copolymer

A flask with attached condenser was charged with 3-acryloxypropyl trimethoxysilane (0.20 g), acrylate-terminated polymer of Preparatory Example 8 (2.0 g), 2,2'-azobis(2-methylbutyronitrile) (20 mg), toluene (5 mL), and methanol (5 mL). The solution was sparged with nitrogen for 10 minutes. After resting for 5 minutes, the solution was sparged for another 5 minutes. The solution was then heated at reflux for 16 hours, after which analysis by NMR suggested 90-95% consumption of the acrylate. The solution was cooled and used without further modification for coating experiments.

Example 1

Synthesis of Poly(2-methyl-2-oxazoline)-Si Brush Copolymer

A flask with attached condenser was charged with 3-acryloxypropyl trimethoxysilane (0.20 g), acrylate-terminated polymer of Preparative Example 1 (2.0 g), 2,2'-azobis(2-methylbutryonitrile) (20 mg), and methanol (10 mL). The solution was sparged with nitrogen for 10 minutes. After resting for 5 minutes, the solution was sparged for another 5 minutes. The solution was then heated at reflux for 16 hours, after which analysis by NMR suggested 90-95% consumption of the acrylate. The solution was cooled and used without further modification for coating experiments.

Example 2

Synthesis of Poly(2-ethyl-2-oxazoline)-Si Brush Copolymer

A flask with attached condenser was charged with 3-acryloxypropyl trimethoxysilane (0.10 g), acrylate-terminated poly(2-ethyl-2-oxazoline) of Preparatory Example 2 (1.0 g), 2,2'-azobis(2-methylbutryonitrile)(10 mg), and methanol (5 mL). The solution was sparged with nitrogen for 10 minutes. After resting for 5 minutes, the solution was sparged for another 5 minutes. The solution was then heated at reflux for 16 hours, after which analysis by NMR suggested 90-95% consumption of the acrylate. The solution was cooled and used without further modification for coating experiments.

Example 3

Synthesis of $C_4F_9$-Poly(2-methyl-2-oxazoline)-Si Brush Copolymer

A flask with attached condenser was charged with 3-acryloxypropyl trimethoxysilane (0.20 g), acrylate-terminated $C_4F_9$-poly(2-methyl-2-oxazoline) of Preparatory Example 5 (2.0 g), 2,2'-azobis(2-methylbutryonitrile)(20 mg), and methanol (10 mL). The solution was sparged with nitrogen for 1.0 minutes. After resting for 5 minutes, the solution was sparged for another 5 minutes. The solution was then heated at reflux for 16 hours, after which analysis by NMR suggested 90-95% consumption of the acrylate. The solution was cooled and used without further modification for coating experiments.

Example 4

Synthesis: of $C_4F_9$—$SO_2$—$NCH_3$-Poly(2methyl-2-oxazoline)-Si Brush Copolymer A flask with attached condenser was charged with 3-acryloxypropyl trimethoxysilane (86 mg), acrylate-terminated polymer of Preparative Example 7 (857 mg), 2,2'-azobis(2-methylbutryonitrile) (9 mg), and methanol (3 mL). The solution was sparged with nitrogen for 10 minutes. After resting for 5 minutes, the solution was sparged for another 5 minutes. The solution was then heated at reflux for 16 hours, after which analysis by NMR suggested 90-95% consumption of the acrylate. The solution was cooled and used without further modification for coating experiments.

Example 5

Preparation and Characterization of Brush Copolymer Coatings

The polymers of the examples above were diluted to a concentration of 20% by weight in methanol. They were then either coated on 2 mil PET film with a Number 22 wire-wound rod (BYK instruments) or directly on glass substrates freshly cleaned with piranha solution (a mixture of concentrated sulfuric acid and hydrogen peroxide solution in a 7:3 volume ratio). The coated films were cured in an oven at 80° C. overnight, then characterized by contact angle analysis.

Example 6

Contact Angle Analysis of the Coatings

Coatings were characterized by dynamic contact angle analysis and by measuring transmission and haze. Dynamic contact angle measurements were observed using a DSA 100 video contact angle goniometer (Kruss Inc.) equipped with a Hamilton syringe having a flat-tipped needle. Deionized water and n-hexadecane were used as the probe fluids. Advancing contact angle and receding contact angle were measured as water was supplied via the syringe into or out of Sessile droplets (drop volume approximately 5 microliters (μL)). All reported values are averages of six contact angle measurements of drops on three different areas of each sample (left and right angles measured for each drop). Reported errors are one standard, deviation.

The results are summarized in Table 1 below.

All the coatings composed of the poly(oxazoline)s that were initiated using polar initiator (methyltriflate or methyl tosilate) had low water (<50°) and hexadecane contact angles (<5°), indicating highly hydrophilic surface (Comparative Example 1 and Examples 2 and 3 in Table 1). Among those, poly(methyl-oxazoline)-based coating (Example 1) showed the highest hydrophilicity, while PEG-based coating (Comparative Example 1) was the least hydrophilic. The coatings composed of the hydrophobic, fluorine containing POx polymers (Examples 3 and 4) yielded an amphophilic character. Both coatings (Examples 3 and 4 in Table 1) had low water contact angles and high hexadecane contact angles.

Table 1 summarizes the contact angle data of the coatings prepared. According to the data, Example 1 yields a more hydrophilic surface than Example 2. When a fluorinated side chain is included, such as in Examples 3 and 4, more hydrophobic surfaces were obtained. When Example 3 and 4 are compared to each other, Example 4 shows higher contact angle values for both water and hexadecane, indicating higher hydrophobicity.

TABLE 1

Contact angle data of selected coatings

| Sample Name | Water | | n-Hexadecane | |
|---|---|---|---|---|
| | Advancing | Receding | Advancing | Receding |
| Comparative Example 1 | 46.1 | 15.2 | Complete wetting of the surface | |
| Example 1 | 22.7 | 11.8 | Complete wetting of the surface | |
| Example 2 | 31.6 | 17.5 | Complete wetting of the surface | |

TABLE 1-continued

Contact angle data of selected coatings

| Sample Name | Water | | n-Hexadecane | |
|---|---|---|---|---|
| | Advancing | Receding | Advancing | Receding |
| 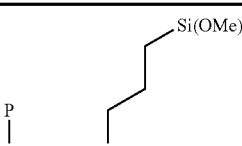 Example 3 | Complete wetting of the surface | | 25.1 | 18.3 |
| 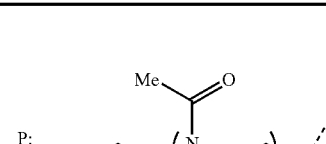 Example 4 | 38.5 | 17.1 | 56.1 | 44.8 |

In Table 1, "w" and "z" are the relative amounts of monomers, which can be calculated from the amounts of starting materials. These representations are not to be interpreted as limiting the copolymers to block copolymers; rather it is simply a representation showing the monomeric moieties in the copolymer, whether it be random, block, or otherwise.

Example 7

Biological Evaluation: Ability of Coatings to Resist Biofilm Formation by *Staphylococcus epidermidis* and *E. coli* in CDC Biofilm Reactor The ability of samples to resist biofilm formation by *S. epidermidis* and *E. coli* in a high shear environment was evaluated using the CDC biofilm reactor (Biosurface Technologies, Bozeman, Mont.) and the procedure described below. For biological evaluation, brush copolymers 1-5 from Table 1 were coated either (1) directly on glass coupons or (2) on PET film as described in Example 5.

For coatings applied directly to glass coupons, three replicate test samples were mounted in CDC reactor coupon holders and placed into a CDC reactor. To remove residual components that could potentially leach from test materials and interfere with the biological, characterization, test samples were rinsed by passing deionized water through the reactor for 18-24 hours at a flow rate of approximately 8 mL/minute with stirring at 130 RPM. Following rinsing, coupon holders were removed from the reactor and the empty reactor was autoclaved at 121° C. for 15 minutes and allowed to cool. Subsequently, the coupon holders carrying sample materials were sterilized by immersing in 70% ethanol and placed into the sterilized CDC reactor. The reactor was filled with approximately 400 mL of sterile dilute Bacto trypic soy broth (TSB, Becton, Dickinson and Co., Sparks, Md.), In these experiments, 10% TSB (3 g TSB per liter) was used. The reactor was inoculated with 0.4 mL of an overnight culture of *S. epidermidis* (ATCC #35984) or *E. coli* (ATCC #25922) grown at 37° C. with agitation in TSB, the stir rate was set to 130 RPM and the system was incubated at 37° C. for 24 hours as a batch culture to allow growth and attachment of bacteria. After 24 hours, sterile 10% TSB was passed through the reactor at a rate of approximately 11.5 mL/min for an additional 24 hours (with continued stirring at 130 RPM and incubation at 37° C.) to facilitate biofilm growth.

To analyze biofilm formation, coupon holders, test samples, and adherent biofilm were removed from the reactor, rinsed by immersing 5 times in phosphate buffered saline (PBS), and stained with 1% crystal violet in water for 1 minute. The coupon holder and samples were then rinsed by dipping 30 times in PBS to remove excess crystal violet. Each coupon was removed from the rod and placed into a 15 mL conical tube (BD Biosciences, Bedford, Mass.) containing 4 mL of ethanol. Crystal violet was eluted by vortexing for approximately 10 seconds, and the absorbance of the ethanol solutions at 590 nm was measured using a spectrophotometer (model LAMBDA 12, Perkin-Elmer Corporation, Waltham, Mass.) to estimate the amount of biofilm adhered to the sample coupons. Triplicate samples were evaluated for each material. Values presented in Table 2 are defined as follows:

$$A_{590} \text{ ratio} = \frac{A_{590} \text{ sample}}{A_{590} \text{ control}}$$

where $A_{590}$ sample=average of triplicate $A_{590}$ values for sample and $A_{590}$ control=average of triplicate $A_{590}$ values for uncoated glass surface $$\sigma_{ratio} = A_{590} \text{ ratio} \sqrt{\left(\frac{\sigma_{sample}}{A_{590} \text{ sample}}\right)^2 + \left(\frac{\sigma_{control}}{A_{590} \text{ control}}\right)^2}$$

where $\sigma_{sample}$=standard deviation of triplicate $A_{590}$ values for sample
and $\sigma_{control}$=standard deviation of triplicate $A_{590}$ values for uncoated glass surface The procedure for evaluation of samples coated on PET film was similar to that described above, with the following changes: instead of testing coupon samples in triplicate, coated film samples were cut, each 2⅛ inch×¾ inch, and attached to 8 blank (no coupon holes) holders using silicone adhesive that was allowed to cure overnight prior to rinsing. For evaluation, samples were stained with crystal violet as described above, then removed from the holder using tweezers and placed into a 15 mL conical tube containing 10 mL ethanol. $A_{590}$ ratio values presented in Table 3 were calculated as above. In the case of coated film samples, however, one replicate each of sample and control material was tested in two separate experiments.

Results:
Coatings Applied Directly to Glass Coupons $A_{590}$ ratio values defined above are summarized in Table 2. $A_{590}$ ratio values less than one correspond to less biofilm on the sample surface compared to the glass control surface.

TABLE 2

| Sample | S. epidermidis | | E. coli | |
|---|---|---|---|---|
| | A590 ratio | σ ratio | A590 ratio | σ ratio |
| Glass Control | 1.00 | | 1.00 | |
| Comparative Example 1 | 0.61 | 0.50 | 0.69 | 0.68 |
| Example 1 | 0.35 | 0.10 | 0.31 | 0.08 |
| Example 2 | 0.66 | 0.42 | 1.03 | 0.31 |

Coatings Applied to PET Film—Hydrophitic Versus Amphiphilic Polymer Coatings $A_{590}$ ratio values defined above are summarized in Table 3. $A_{590}$ ratio values less than one correspond to less biofilm on the sample surface compared to the primed PET (polyethylene terapthalate) control surface.

TABLE 3

| Sample | S. epidermidis | | E. coli | |
|---|---|---|---|---|
| | A590 ratio experiment 1 | A590 ratio experiment 2 | A590 ratio experiment 1 | A590 experiment 2 |
| Primed PET | 1.00 | 1.00 | 1.00 | 1.00 |
| Example 1 | 0.18 | 0.06 | 1.68 | 1.34 |
| Example 3 | 1.05 | 0.51 | 1.79 | 1.39 |
| Example 4 | 0.31 | 0.26 | 0.45 | 0.59 |

While biofilms can be formed by a single species of microorganism, often they are composed of a community of different types of microorganisms. Since different microorganism utilize different mechanisms to attach to a substrate, it is important to employ representative species of microorganisms when evaluating the ability of a material to resist biofilm formation. For these biofilm studies, S. epidermidis and E. coli were selected as representative examples of gram-positive and gram-negative bacteria, respectively.

Table 2 summarizes the biofilm formation data comparison among the non-fluorinated or hydrophilic surfaces. Among the surfaces tested, Example 1 shows the lowest biofilm formation across both species.

Table 3 summarizes the biofilm formation data comparison of Example 1 (purely hydrophilic coating) to Examples 3 and 4 (amphiphilic coatings). While Example 1 shows low biofilm formation for S. epidermidis, it does not perform as well against E. coli. However, when a fluorinated side chain is incorporated to the same polymer yielding Example 4, low biofilm formation is observed for both S. epidermidis and E. coli. This comparison shows that, to be able to prevent biofilm formation across different species, an amphiphilic balance may be preferred. This is further supported by comparing Example 3 to Example 4. While both examples have a similar composition, Example 4 yields a more hydrophobic surface with the aid of the sulfonamide group, (as observed from the contact angle analysis in Table 1), providing the necessary amphiphilicity for the system to be more biofilm resistant.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:
1. A copolymer derived from a monomer mixture comprising monomers having the formulas:

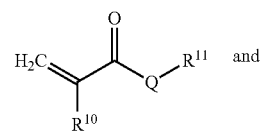

(A) and

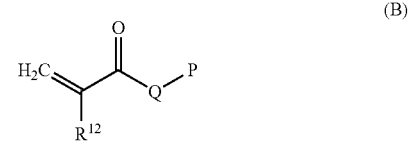

(B)

wherein:
Q is O or N;
$R^{10}$ is H or $CH_3$;
$R^{11}$ is an organic group comprising a hydrolyzable silyl group;
$R^{12}$ is H or $CH_3$; and
P is:

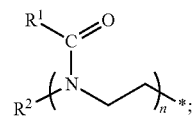

wherein:
R$^1$ is selected from H, an alkyl group, an aryl group, and a combination thereof;
R$^2$ is selected from an alkyl group, an aryl group, a combination thereof, and a R$^f$—Y—(CH$_2$)$_x$— group;
R$^f$ is a perfluorinated alkyl group;
Y is selected from a bond, —S(O)$_2$—N(CH$_3$)—, —S(O)$_2$—N(CH$_2$CH$_3$)—, —S(O)$_2$—O—, —S(O)$_2$—, —C(O)—, —C(O)—S—, —C(O)—(O)—O—, —C(O)—NH—, —C(O)—N(CH$_3$)—, —C(O)—N(CH$_2$CH$_3$)—, —(CH$_2$CH$_2$O)$_y$—, —O—, and —O—C(O)—CH=CH—C(O)—O—;
n is an integer of greater than 2;
x is an integer of at least 2; and
y is an integer of at least 1.

2. The copolymer of claim 1 wherein R$^{11}$ is —Z—Si(R$^{13}$)$_3$ wherein:
each R$^{13}$ is independently selected from an alkyl group, an aryl group, a combination thereof, and a hydrolyzable group;
at least one R$^{13}$ is a hydrolyzable group; and
Z is selected from an alkylene group, an arylene group, and a combination thereof, optionally including —O—, —C(O)—, —NH—, —S—, or a combination thereof, within the chain.

3. The copolymer of claim 2 wherein the hydrolyzable group is selected from a halo, a (C1-C4)alkoxy group, and a (C1-C4)acyloxy group.

4. The copolymer of claim 2 wherein Z is selected from a (C1-C20)alkylene group, a (C6-C12)arylene group, and a combination thereof, optionally including —O—, —C(O)—, —NH—, —S—, or a combination thereof, within the chain.

5. The copolymer of claim 1 wherein R$^1$ is selected from H, methyl, and ethyl.

6. The copolymer of claim 1 wherein R$^2$ is a R$^f$—Y—(CH$_2$)$_x$— group.

7. The copolymer of claim 6 wherein Y is selected from a bond, —S(O)$_2$—N(CH$_3$)—, —C(O)—NH—, and —(CH$_2$CH$_2$O)$_y$—.

8. The copolymer of claim 6 wherein R$^f$ is a perfluorinated (C1-C8)alkyl group.

9. The copolymer of claim 1 wherein n is an integer of greater than 10.

10. The copolymer of claim 1 wherein x is an integer no greater than 20.

11. The copolymer of claim 1 wherein y is an integer no greater than 20.

12. A brush copolymer derived from a monomer mixture comprising monomers having the formulas:

(A)

$$H_2C=C(R^{10})-C(O)-Q-R^{11}$$

and (B)

$$H_2C=C(R^{12})-C(O)-Q-P$$

wherein:
Q is O or N;
R$^{10}$ is H or CH$_3$;
R$^{11}$ is —Z—Si(R$^{13}$)$_3$;
R$^{12}$ is H or CH$_3$;
each R$^{13}$ is independently selected from an alkyl group, an aryl group, a combination thereof, and a hydrolyzable group;
at least one R$^{13}$ is a hydrolyzable group;
Z is selected from an alkylene group, an arylene group, and a combination thereof, optionally including —O—, —C(O)—, —NH—, —S—, or a combination thereof, within the chain; and
P is:

$$R^2-[N(C(O)R^1)-CH_2CH_2]_n-*$$

wherein:
R$^1$ is selected from H, an alkyl group, an aryl group, and combinations thereof;
R$^2$ is R$^f$—Y—(CH$_2$)$_x$— group;
R$^f$ is a perfluorinated (C1-C8)alkyl group;
Y is a bond, —S(O)$_2$—N(CH$_3$)—, —C(O)—O—, —C(O)—NH—, or —(CH$_2$CH$_2$O)$_y$—;
n is an integer from 20 to 100;
x is an integer from 2 to 20; and
y is an integer from 1 to 20.

13. A composition comprising a copolymer of claim 1 and a solvent.

14. A method of coating a substrate to improve biofilm resistance of the substrate, the method comprising coating at least one surface of the substrate with the composition of claim 13.

15. An article comprising a substrate, wherein the substrate comprises at least one surface having a layer comprising a copolymer of claim 1 disposed thereon.

16. The copolymer of claim 1, wherein the copolymer has a weight average molecular weight of at least 2,000 g/mol.

17. The copolymer of claim 1, wherein n is an integer from 20 to 100.

18. The copolymer of claim 1, wherein the copolymer is derived from at least 1 wt-% of monomer A.

19. The copolymer of claim 1, wherein the copolymer is derived from no more than 50 wt-% of monomer A.

20. The copolymer of claim 1, wherein monomer B is of the formula:

$$R^2-[N(C(O)R^1)-CH_2CH_2]_n-R^3$$

wherein:
R$^1$ is selected from H, an alkyl group, an aryl group, and combinations thereof;
R$^2$ is R$^f$—Y—(CH$_2$)$_x$—;
R$^3$ is a (meth)acryloyloxy group or a (meth)acryloylamino group;
R$^f$ is a perfluorinated alkyl group;
Y is selected from a bond, —S(O)$_2$—N(CH$_3$)—, —S(O)$_2$—N(CH$_2$CH$_3$)—, —S(O)$_2$—O—, —S(O)$_2$—, —C(O)—, —C(O)—S—, —C(O)—O—, —C(O)—NH—, —C(O)—N(CH$_3$)—, —C(O)—N $(CH_2CH_3)-$, $-(CH_2CH_2O)_y-$, $-O-$, and $-O-C(O)-CH=CH-C(O)-O-$;

n is an integer of greater than 10;
x is an integer from 2 to 20; and
y is an integer from at least 1.

* * * * *

UNITED STATES PATENT AND TRADEMARK OFFICE
CERTIFICATE OF CORRECTION

PATENT NO.        : 9,556,340 B2
APPLICATION NO.   : 14/649400
DATED             : January 31, 2017
INVENTOR(S)       : Semra Colak Atan It is certified that error appears in the above-identified patent and that said Letters Patent is hereby corrected as shown below:

In the Specification

Column 1,
Line 40, delete "biofoulmg" and insert -- biofouling --, therefor.
Line 49, delete "biofoulmg" and insert -- biofouling --, therefor.
Line 57, delete "polyethylene" and insert -- poly(ethylene --, therefor.

Column 2,
Line 47, delete "thereof" and insert -- thereof, --, therefor.

Column 3,
Line 26, delete "aryi" and insert -- aryl --, therefor.

Column 4,
Line 6, delete "thai" and insert -- that --, therefor.
Line 7, delete "aikane" and insert -- alkane --, therefor.
Lines 15 & 16, delete "1,4-cyclohexydimethylene." and insert -- 1,4-cyclohexyldimethylene. --, therefor.
Line 60, delete "atoms. 6 to 16 carbon atoms." and insert -- atoms, 6 to 16 carbon atoms, --, therefor.

Column 6,
Line 4, delete "list," and insert -- list --, therefor.
Line 24, delete "titan" and insert -- than --, therefor.

Column 7,

Lines 16 & 17, after " 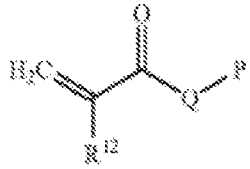 " insert -- . --.

Signed and Sealed this
Eighteenth Day of April, 2017

Michelle K. Lee
*Director of the United States Patent and Trademark Office*

CERTIFICATE OF CORRECTION (continued)
U.S. Pat. No. 9,556,340 B2

Column 7,
Line 25, delete "etc)." and insert -- etc.). --, therefor.
Line 60, delete "chain, in" and insert -- chain. In --, therefor.
Line 62, delete "—C(O)Q-group." and insert -- —C(O)Q— group. --, therefor.

Column 8,
Line 22, delete "—S(O)$_2$—N(CH$_2$CH$_3$," and insert -- —S(O)$_2$—N(CH$_2$CH$_3$)—, --, therefor.
Line 32, delete "group, in" and insert -- group. In --, therefor.
Line 66, delete "attachment," and insert -- attachment --, therefor.

Column 9,
Line 11, delete "bond." and insert -- bond, --, therefor.

Column 11,

Lines 14-18, after "  " insert -- , --.

Lines 19-23, after " 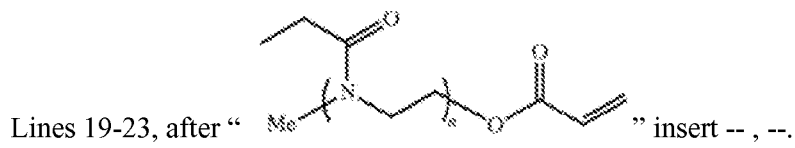 " insert -- , --.

Lines 24-29, after " 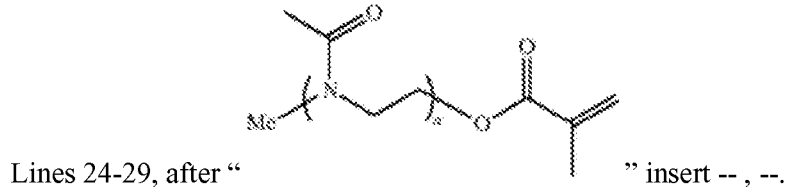 " insert -- , --.

Lines 30-32, after " 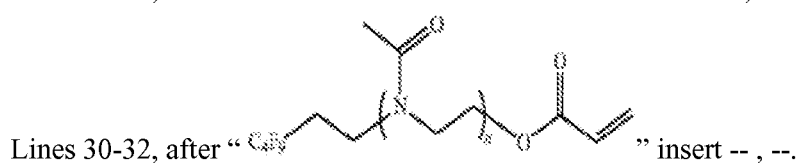 " insert -- , --.

Lines 33-37, after " 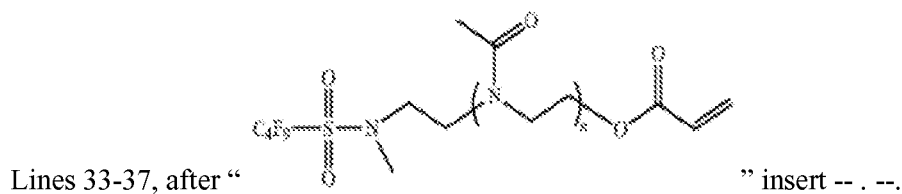 " insert -- . --.

Column 12,
Line 31, delete "—(CH$_2$CH$_2$O)$_y$—," and insert -- —(CH$_2$CH$_2$O)$_y$—; --, therefor.

Column 13,
Line 24, delete "photo initiator" and insert -- photoinitiator --, therefor.
Line 27, delete "(e:g.," and insert -- (e.g., --, therefor.
Line 27, delete "ether)," and insert -- ether). --, therefor.

CERTIFICATE OF CORRECTION (continued)
U.S. Pat. No. 9,556,340 B2

Column 14,
Line 15, delete "art" and insert -- an --, therefor.
Line 50, delete "acrylonitriie" and insert -- acrylonitrile --, therefor.
Line 61, delete "R" and insert -- $R^{13}$ --, therefor.

Column 15,
Line 11, delete "he" and insert -- be --, therefor.
Line 23, delete "of" and insert -- or --, therefor.

Column 16,
Lines 11 & 12, delete "—C(O)—O," and insert -- —C(O)—O—, --, therefor.
Line 43, delete "C(O)—," and insert -- —C(O)—, --, therefor.
Line 49, delete "$R^f$—Y—(CH$_2$)$_x$-group." and insert -- $R^f$—Y—(CH$_2$)$_x$— group. --, therefor.
Line 55, delete "$R^f$is" and insert -- $R^f$ is --, therefor.

Column 17,
Line 33, delete "wherein;" and insert -- wherein: --, therefor.
Line 50, delete "having," and insert -- having --, therefor.

Column 18,
Line 25, delete "wherein;" and insert -- wherein: --, therefor.
Line 64, delete "3 Å" and insert -- 3Å --, therefor.
Line 65, delete "3 Å" and insert -- 3Å --, therefor.

Columns 19 & 20,

Lines 3 & 4, after " 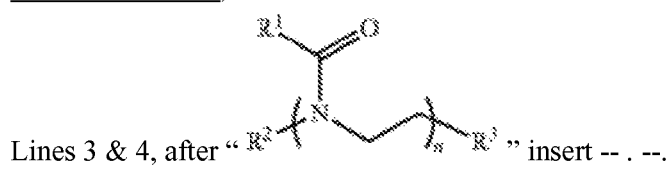 " insert -- . --.

Column 25,

Line 31-35, after " 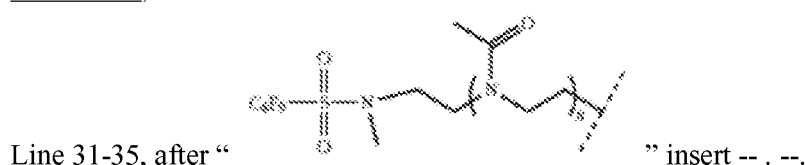 " insert -- . --.
Line 40, delete "Brash" and insert -- Brush --, therefor.

Column 26,
Line 12, delete "2,2'-azobis(2-methylbutryonitrile)(10 mg)," and insert
-- 2,2'-azobis(2- methylbutyronitrile) (10 mg), --, therefor.
Line 29, delete "2,2'-azobis(2-methylbutryonitrile)(20 mg)," and insert
-- 2,2'-azobis(2- methylbutyronitrile) (20 mg), --, therefor.
Line 40, delete "Synthesis:" and insert -- Synthesis --, therefor.
Line 40, delete "Poly(2methyl-2-" and insert -- Poly(2-methyl-2- --, therefor.

Column 27,
Line 13, delete "Sessile" and insert -- sessile --, therefor.
Line 17, delete "standard," and insert -- standard --, therefor.

Column 28,
Line 9, delete "amphophilic" and insert -- amphiphilic --, therefor.

Column 29,
Line 58, delete "biological," and insert -- biological --, therefor.

Column 31,
Line 16, delete "$2^{1}/_{8}$ inch×¾ inch," and insert -- $2\ ^{1}/_{8}$ inch × ¾ inch, --, therefor.
Line 41, delete "Hydrophitic" and insert -- Hydrophilic --, therefor.

Column 32,
Line 11, delete "Example 4 ," and insert -- Example 4, --, therefor.
Line 16, delete "Example 4 ." and insert -- Example 4. --, therefor.

In the Claims

Column 33,
Lines 10 & 11, in Claim 1, delete "—C(O)—(O)—O—," and insert -- —C(O)—O—, --, therefor.
Line 12, in Claim 1, delete "—(CH$_2$CH$_2$O)$_y$—,—O—," and insert -- —(CH$_2$CH$_2$O)$_y$—, —O—, --, therefor.
Line 31, in Claim 4, delete "including—O—," and insert -- including —O—, --, therefor.